(12) United States Patent
Sonnewald et al.

(10) Patent No.: US 6,806,085 B1
(45) Date of Patent: Oct. 19, 2004

(54) 2-DEOXYGLUCOSE-6-PHOSPHATE (2-DOG-6-P) PHOSPHATASE DNA SEQUENCES AS SELECTION MARKER IN PLANTS

(75) Inventors: Uwe Sonnewald, Quedlinburg (DE); Marcus Ebneth, Berlin (DE)

(73) Assignee: IPK Gatersleben, Gatersleben (DE)

( * ) Notice: Subject to any disclaimer, the term of this patent is extended or adjusted under 35 U.S.C. 154(b) by 0 days.

(21) Appl. No.: 09/558,284

(22) Filed: Apr. 25, 2000

Related U.S. Application Data

(63) Continuation of application No. PCT/EP98/02069, filed on Apr. 9, 1998.

(30) Foreign Application Priority Data

Apr. 9, 1997 (EP) .............................................. 97105855

(51) Int. Cl.$^7$ ........................... C12N 15/82; C12N 15/52
(52) U.S. Cl. ........................................ 435/468; 800/288
(58) Field of Search .............................. 435/468, 320.1, 435/419; 800/288, 278, 298

(56) References Cited

FOREIGN PATENT DOCUMENTS

| | | | | |
|---|---|---|---|---|
| EP | 0289478 A2 | 11/1988 | ........... | C12N/15/00 |
| JP | 52007423 A2 | 1/1977 | | |
| WO | WO 94/20627 | 9/1994 | ........... | C12N/15/82 |
| WO | WO 96/31612 | 10/1996 | ........... | C12N/15/82 |

OTHER PUBLICATIONS

Abel, P.P. et al., "Delay of Disease Development in Transgenic Plants That Express the Tobacco Mosaic Virus Coat Protein Gene," *Science*, 232, 738–743 (1986).
An, G. et al., "New Cloning Vehicles for Transformation of Higher Plants," *The EMBO Journal*, 4, 277–284 (1985).
Bayley, C. C. et al, "Exchange of Gene Activity in Transgenic Plants Catalyzed by the Cre–lox Site–Specific Recombination System," *Plant Molecular Biology*, 18, 353–361 (1992).
Becker, D. et al., "New Plant Binary Vectors with Selectable Markers Located Proximal to the Left T–DNA Border," *Plant Molecular Biology*, 20, 1195–1197 (1992).
Bevan, M., "Binary Agrobacterium Vectors for Plant Transformation," *Nucleic Acids Research*, 12, 8711–8721 (1984).
Braun, H.P., "The General Mitochondrial Processing Peptidase from Potato is an Integral Part of Cytochrome C Reductase of the Respiratory Chain," *The EMBO Journal*, 11, 3219–3227 (1992).
Bytebier, B. et al., "T–DNA Organization in Tumor Cultures and Transgenic Plants of the Monocotyledon *Asparagu Officinalis*," *Proc. Natl. Acad. Sci. USA*, 84, 5345–5349 (1987).
Chan, M.T. et al., "Agrobacterium–mediated Production of Transgenic Rice Plants Expressing a Chimeric α–amylase Promoter/β–glucuronidase Gene," *Plant Molecular Biology*, 22, 491–506 (1993).

Christou, P., "Transformation Technoloy," *Trends in Plant Science*, 1, 423–431 (1996).
Datema, R. et al., "Formation of 2–Deoxyglucose–Containing Lipid–Linked Oligosaccharides," *Eur. Biochem.*, 90, 505–516 (1978).
De Block, M., et al., "Engineering Herbicide Resistance in Plants by Expression of a Detoxifying Enzyme," *The EMBO Journal*, 6, 2513–2518 (1987).
Deblaere, R. et al., "Efficient Octopine Ti Plasmid–derived Vectors for Agrobacterium–mediated Gene Transfer to Plants," *Nucleic Acids Research*, 13, 4777–4788 (1985).
Farrar, J.F. et al., "Carbon Import into Barley Roots: Effects of Sugars and Relation to Cell Expansion," *Journal of Experimental Botany*, 46, 1859–1865 (1995).
de Feyter, R. et al., "A Ribozyme Gene and an Antisense Gene are Equally Effective in Conferring Resistance to Tobacco Mosaic Virus on Transgenic Tobacco," *Mol. Gen. Genet.*, 250, 329–338 (1996).
Fraley, R.T. et al., "Genetic Transformation in Higher Plants," *CRC Critical Reviews in Plant Sciences*, 4, 1–46.
Franck, A. et al., "Nucleotide Sequence of Cauliflower Mosaic Virus DNA," *Cell*, 21, 285–294 (1980).
Gallie, D.R. et al., "A Comparison of Eukaryotic Viral 5'–leader Sequences as Enhancers of mRNA Expression in vivo," *Nucleic Acids Research*, 15, 8693 (1987).
Gancedo, J.M.et al., "Carbon Catabolite Repression in Yeast," *FEBS*, 206, 297–313 (1992).
Gatz, C. et al., "Regulation of a Modified CaMV 35S Promoter by the Tn10–encoded Tet Repressor in Transgenic Tobacco," *Mol. Gen. Genet*, 227, 229–237 (1991).
Gielen, J. et al., "The Complete Nucleotide Sequence of the TL–DNA of the *Agrobacterium tumefaciens* Plasmid p TiAch5," *The EMBO Journal*, 3, 835–846 (1984).
Gould, J. et al., "Transformation of *Zea Mays* L. Using *Agrobacterium tumefaciens* and the Shoot Apex," *Plant Physiol.*, 95, 426–434 (1991).

(List continued on next page.)

*Primary Examiner*—Phuong T. Bui
*Assistant Examiner*—Cynthia Collins
(74) *Attorney, Agent, or Firm*—Fish & Neave; James F. Haley; Li Su

(57) ABSTRACT

Recombinant DNA molecules are described which contain a DNA sequence encoding a protein with the biological activity of a 2-deoxyglucose-6-phosphate (2-DOG-6-P) phosphatase and being under the control of regulatory sequences of a promoter active in plants and transcription-termination and/or poyladenylation signals. Also, vectors and hosts are described which contain the recombinant DNA molecules according to the invention. Furthermore, processes for producing transformed plant cells and plants using the described recombinant DNA molecules and vectors are provided. The invention also describes transgenic plants, their harvest products and propagation material as well as plant cells and tissues containing the recombinant DNA molecules or vectors according to the invention or having been produced by the process according to the invention.

11 Claims, 12 Drawing Sheets

OTHER PUBLICATIONS

Herbers, K. et al., "Manipulating Metabolic Partitioning in Transgenic Plants," *TIBTECH* 14, 198–205 (1996).

Heredia, C.F. et al., "Metabolic Studies with 2–Deoxyhexoses, I. Mechanisms of Inhibition of Growth and Fermentation in Baker's Yeast," *Biochim. Biophys. Acta,* 86, 216–223 (1964).

Herrera–Estrella, L. et al., "Chimeric Genes as Dominant Selectable Markers in Plant Cells," *The EMBO Journal,* 2, 987–995 (1983).

Hiei, Y. et al., "Efficient Transformation of Rice (*Oryza sativa L.*) Mediated by Agrobacterium and Sequence Analysis of the Boundaries of the T–DNA," *The Plant Journal,* 6, 271–282 (1994).

Höfgen, R. et al., "Storage of Competent Cells for Agrobacterium Transformation," *Nucleic Acids Research,* 16, 9877 (1988).

Hoekema, A. et al., "Non–oncogenic T–region Derived Plant Vectors in the Agrobacterium Binary System," The Binary Plant Vector System, Offsetdrukkerij Kanters B.V., Alblasserdam, 63–71 (1985).

Holsters, M. et al., "Transfection and Transformation of *Agrobacterium tumefaciens,*" *Molec. Gen. Genet.* 163, 181–187 (1978).

Jähne, A. et al., "Genetic Engineering of Cereal Crop Plants: A Review," *Euphytica,* 85, 35–44 (1995).

Kapros, T. et al., "A Short Histone H3 Promoter from Alfalfa Species Expression in S–phase Cells and Meristems," *In Vitro Cell. Dev. Biol.,* 29, 27–32 (1993).

Kratky, Z. et al., "Mechanism of 2–Deoxy–D–glucose Inhibition of Cell–Wall Polysaccharide and Glycoprotein Biosyntheses in *Saccharomyces cerevisiae,*" *Eur. J. Biochem.* 54, 459–467 (1975).

Lehrach, H. et al., "RNA Molecular Weight by Gel Electrophoresis Under Denaturing Conditions, a Critical Reexamination," *Biochemistry,* 16, 4743–4751 (1977).

Li, X. et al., "Factors Influencing Agrobacterium–mediated Transient Expression of gusA in Rice," *Plant Molecular Biology,* 20, 1037–1048 (1992).

Lloyd, A.M. et al., "Functional Expression of the Yeast FLP/FRT Site–specific Recombination System in *Nicotiana tabacum,*" *Mol. Gen. Genet.* 242, 653–657 (1994).

Lobo, Z. et al., "Resistance to 2–Deoxyglucose in Yeast: A Direct Selection of Mutants Lacking Glucose–Phosphorylating Enzymes," *Molec. Gen. Genet.* 157, 297–300 (1977).

Logemann, J. et al., "Improved Method for the Isolation of RNA from Plant Tissues," *Analytical Biochemistry,* 163, 16–20 (1987).

Lyznik, L.A. et al., "Stable Co–transformation of Maize Protoplasts with gusA and neo Genes," *Plant Molecular Biology,* 13, 151–161 (1989).

Maeser, S. et al., "The Gin Recombinase of Phage Mu can Catalyse Site–Specific Recombination in Plant Protoplasts," *Mol. Gen. Genet.,* 230, 170–176 (1991).

Maheshwari, N. et al., "In Vitro Culture of Wheat and Genetic Transformation—Retrospect and Prospect," *Critical Reviews in Plant Sciences,* 14, 149–178 (1995).

Mooney, P.A., "*Agrobacterium tumefaciens*–gene Transfer into Wheat Tissues," *Plant Cell Tissue & Organ Culture,* 25, 209–218 (1991).

Murashige, T. et al., "A Revised Medium for Rapid Growth and Bio Assays with Tobacco Tissue Cultures," *Physiologia Plantarum* 15, 473–497 (1962).

Novak, S. et al., "2–Deoxy–D–glucose Resistant Yeast with Altered Sugar Transport Activity," *FEBS Letters,* 269, 202–204 (1990).

Oeller, P.W. et al., "Reversible Inhibition of Tomato Fruit Senescence by Antisense RNA," *Science,* 254, 437–439 (1991).

Onouchi, H. et al., "Operation of an Efficient Site–specific Recombination System of *Zygosaccharomyces rouxii* in Tobacco Cells," *Nucleic Acids Research,* 19, 6373–6378 (1991).

Peng, J. et al., "Inheritance of gusA and neo Genes in Transgenic Rice," *Plant Molecular Biology,* 27, 91–104 (1995).

Pietrzak, M. et al., "Expression in Plants of Two Bacterial Antibiotic Resistance Genes After Protoplast Transformation with a New Plant Expression Vector," *Nucleic. Acids Research* 14, 5857–5868 (1986).

Poirer, Y. et al., "Polyhydroxybutyrate, a Biodegradable Thermoplastic, Produced in Transgenic Plants," *Science,* 256, 520–523 (1992).

Potrykus, I., "Gene Transfer to Plants: Assessment and Perspectives," *Physiologia Plantarum,* 79, 125–134 (1990).

Raineri, D.M. et al., "Agrobacterium–Mediated Transformation of Rice (*Oryza Sativa L.*)," *Bio/Technology,* 8, 33–38 (1990).

Randez–Gil, F. et al., "$DOG^R1$ and $DOG^R2$: Two Genes from *Saccharomyces cerevisiae* that Confer 2–Deoxyglucose Resistance when Overexpressed," *Yeast,* 11, 1233–1240 (1995).

Reiss, B. et al., "RecA Protein Stimulates Homologous Recombination In Plants," *Proc. Natl. Acad. Sci. USA* 93, 3094–3098 (1996).

Rocha–Sosa, M. et al., "Both Developmental and Metabolic Signals Activate the Promoter of a Class I Patatin Gene," *The EMBO Journal,* 8, 23–29 (1989).

Rogers, S.O. et al., "Extraction of DNA from Milligram Amounts of Fresh, Herbarium and Mummified Plant Tissues," *Plant Molecular Biology,* 5, 69–76 (1985).

Sanz, P. et al., "Molecular Characterization of a Gene that Confers 2–Deoxyglucose Resistance in Yeast," *Yeast,* 10, 1195–1202 (1994).

Schmidt, M.F.G. et al., "Metabolism of 2–Deoxy–2–fluoro–D–[$^3$H]glucose and 2–Deoxy–2–fluoro–D[$^3$H]mannose in Yeast and Chick–Embryo Cells," *Eur. J. Biochem.,* 87, 55–68 (1978).

Sonnewald, U., "Expression of *E. coli* Inorganic Pyrophosphatase in Transgenic Plants Alters Photoassimilate Partitioning," *The Plant Journal,* 2, 571–581 (1992).

Sonnewald, U. et al., "Transgenic Tobacco Plants Expressing Yeast–derived Invertase in Either the Cytosol, Vacuole or Apoplast; a Powerful Tool for Studying Sucrose Metabolism and Sink/Source Interactions," *The Plant Journal,* 1, 95–106 (1991).

Stalker, D.M. et al., "Herbicide Resistance in Transgenic Plants Expressing a Bacterial Detoxification Gene," *Science,* 242, 419–423 (1988).

Stenlid, G., "Species Differences between Plant Roots in the Reaction to Inhibitory Sugars," *Physiologia Plantarum* 12, 218–235 (1959).

Stockhaus, J. et al., "Correlation of the Expression of the Nuclear photosynthetic Gene ST–LS1 with the Presence of Chlorophasts," *The EMBO Journal,* 8, 2445–2451 (1989).

Stockhaus, J. et al., "Analysis of Cis–active Sequences Involved in the Leaf–specific Expression of a Potato Gene in Transgenic Plants," *Proc. Natl. Acad. Sci. USA,* 84, 7943–7947 (1987).

2-DEOXYGLUCOSE-6-PHOSPHATE (2-DOG-6-P) PHOSPHATASE DNA SEQUENCES AS SELECTION MARKER IN PLANTS

This application is a continuation of International Application PCT/EP98/02069, filed Apr. 9, 1998, which designates the United States.

BACKGROUND OF THE INVENTION

It is possible to specifically integrate foreign genes into the plant genome by genetic engineering. This process is referred to as transformation and the resulting plants as transgenic plants. The main objectives are plant protection and an increase in quality of the harvest products. Examples of plant protection measures are: (i) herbicide-tolerant plants (DE-A-3701623; Stalker (1988) Science 242, 419), (ii) insect-resistant plants (Vaek (1987) Plant Cell 5, 159–169), (iii) virus-resistant plants (Powell (1986) Science 232, 738–743) and (vi) ozone-resistant plants (Van Camp (1994) BioTech. 12, 165–168). Examples of increase in quality are: (i) decrease in perishability of fruits (Oeller (1991) Science 254, 437–439), (ii) increase in starch production in potato tubers (Stark (1992) Science 242, 419), (iii) modification in starch (Visser (1991) Mol. Gen. Genet. 225, 289–296) and lipid composition (Voelker (1992) Science 257, 72–74) and (iv) production of polymers foreign to the plant (Poirer (1992) Science 256, 520–523). A prerequisite for producing transgenic plants is the availability of suitable transformation systems and the existence of selectable marker allowing the identification of successfully transformed plant cells.

For the transformation there are presently several methods available. The method most frequently used for transforming dicotyledonous plants is the Agrobacterium-mediated gene transfer. Here, use is made of the natural capability of the soil bacterium of integrating genetic material into the plant genome. Further suitable methods are, e.g., protoplast transformation by polyethylene glycol induced DNA transfer, electroporation, sonication or microinjection as well as the transformation of intact cells or tissues by micro- or macroinjection into tissues or embryos, tissue electroporation, incubation of dry embryos in DNA-containing solution, vacuum infiltration of seed and the biolistic gene transfer.

Since quite independently of the method of transformation only few cells carry the desired properties, a selectable marker is integrated into the plant genome by conventional methods besides the target gene which allows the identification of transgenic cells. Presently, mainly genes are used for selecting transformed plant cells that mediate a herbicide or antibiotics tolerance. Suitable resistance genes are, e.g., the bar gene from Streptomyces hygroscopicus, which mediates resistance to the total herbicide phosphinothricine (De Block (1987) EMBO J. 6, 2513–2518), or the nptII gene from the transposon Tn5 of Escherichia coli, which confers resistance to the antibiotic kanamycin (Herrera-Estrella (1983) EMBO J. 2, 987–995). Depending on the plant species, the methods mentioned are not always effective and frequently negatively affect plant regeneration. Also, the use of genes mediating antibiotics resistances is undesired in the foodstuff sector. Furthermore, it is necessary to manipulate several enzymatic steps to control complex metabolic processes, i.e., it is essential in the area of "metabolic engineering" to allow for the possibility of multiple transformations of transgenic plants. The above-mentioned reasons have prompted the intensive search for other selectable markers. Despite intensive efforts only few new markers have been successfully used for selecting transformed plant cells. On the basis of the expression of a mannose-6-phosphate isomerase a positive selection on mannose-containing culture media for transformed plant cells could be established (WO 94/20627). Another process makes use of the capability of a deaminase from Aspergillus terreus to detoxicate the insecticide Blasticidin S (Tamura (1995) Biosci. Biotechnol. Biochem. 59, 2336–2338).

SUMMARY OF THE INVENTION

The present invention relates to the use of DNA sequences encoding a protein with the biological activity of a 2-deoxyglucose-6-phosphate (2-DOG-6-P) phosphatase as selection marker in plant cells for selecting transformed plants. Furthermore, the invention relates to recombinant DNA molecules containing such DNA sequences, with the latter being operably linked to regulatory sequences of a promoter active in plants and transcription termination and/or polyadenylation signals. Also, vectors, host cells and kits are described containing such recombinant DNA molecules, as well as plant cells and plants transformed with the recombinant DNA molecules. The present invention furthermore relates to processes for producing transgenic plants which due to the introduction of the above-described recombinant DNA molecules can be selected on media containing 2-deoxyglucose. Finally, the present invention relates to transgenic plants, plant cells and tissues containing the DNA molecule according to the invention or being obtained by the process described above, as well as harvest products and propagation material of the transgenic plants described.

BRIEF DESCRIPTION OF THE DRAWINGS

FIG. 3). Fragment C (192 bp): Contains the polyadenylation signal of gene 3 of the T-DNA of the Ti-Plasmids pTiACH5. Fragments A to C were cloned via EcoRI/HindIII into the binary vector BIN19 (Bevan (1984) Nucl. Acid Res. 12, 8711).

Northern analysis of transgenic tobacco plants of the line 35S-DOG. Whole RNA was isolated from tobacco, leaves, separated by gel electrophoresis and transferred onto a nylon membrane. Hybridization was performed with a radioactively labeled coding region of the DOG$^R$1 gene. 20 μg RNA were applied per lane. Lanes 1–9, independently transformed plants of the line 35S-DOG; lane 10, untransformed control.

Figure 7:
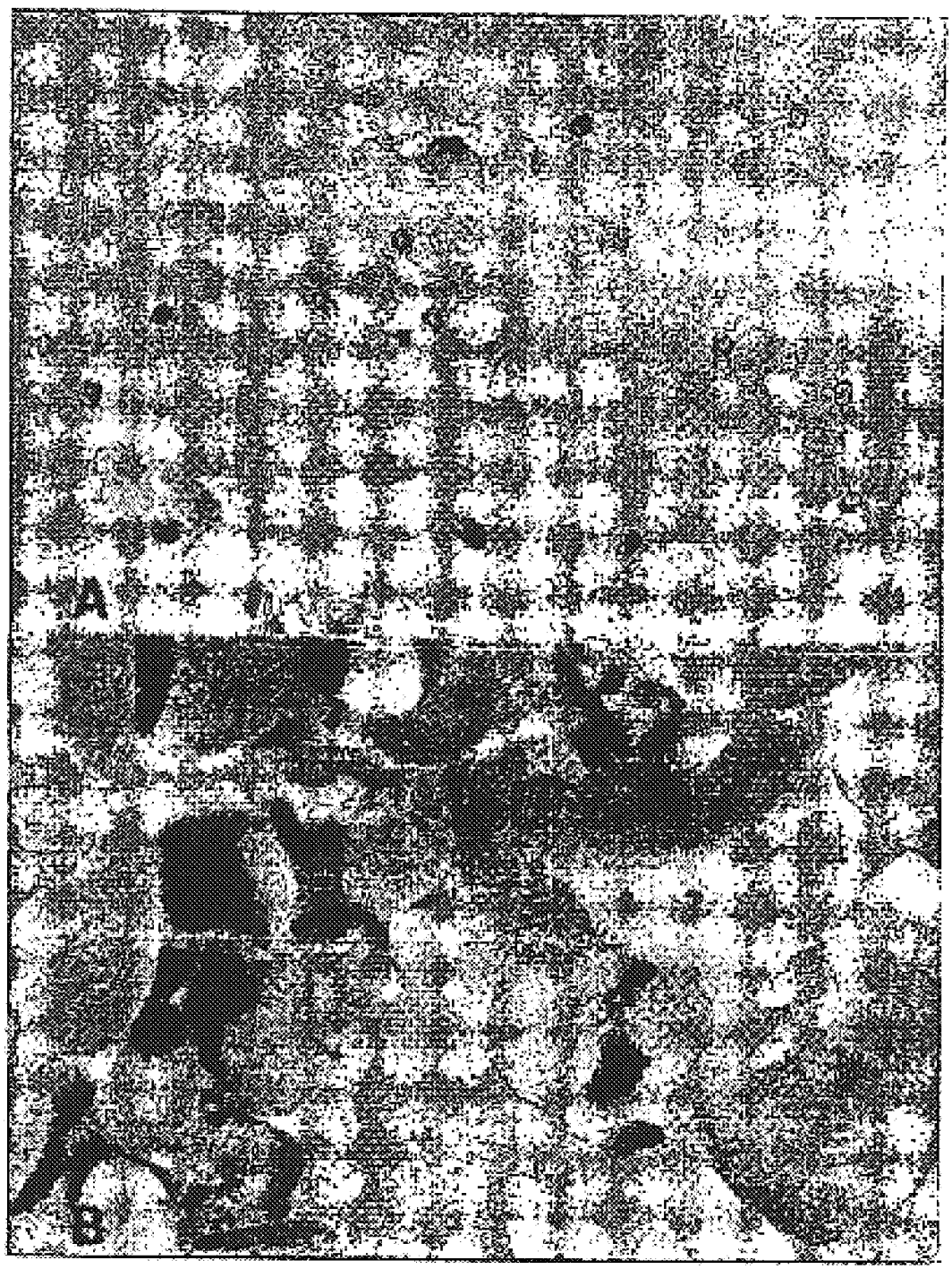

FIG. 7 Detection of the DOGR1 gene mediated resistance in the progeny of transgenic potato plants.

Seeds of *Nicotiana tabacum* Var. *Samsun* NN were sterilized and placed on 0.05% 2-DOG containing MS medium. A: four weeks old seedlings of an untransformed plant; B: four weeks old seedlings of a plant expressing the DOG$^R$1 gene under the control of the 35S promoter.

Figure 8:
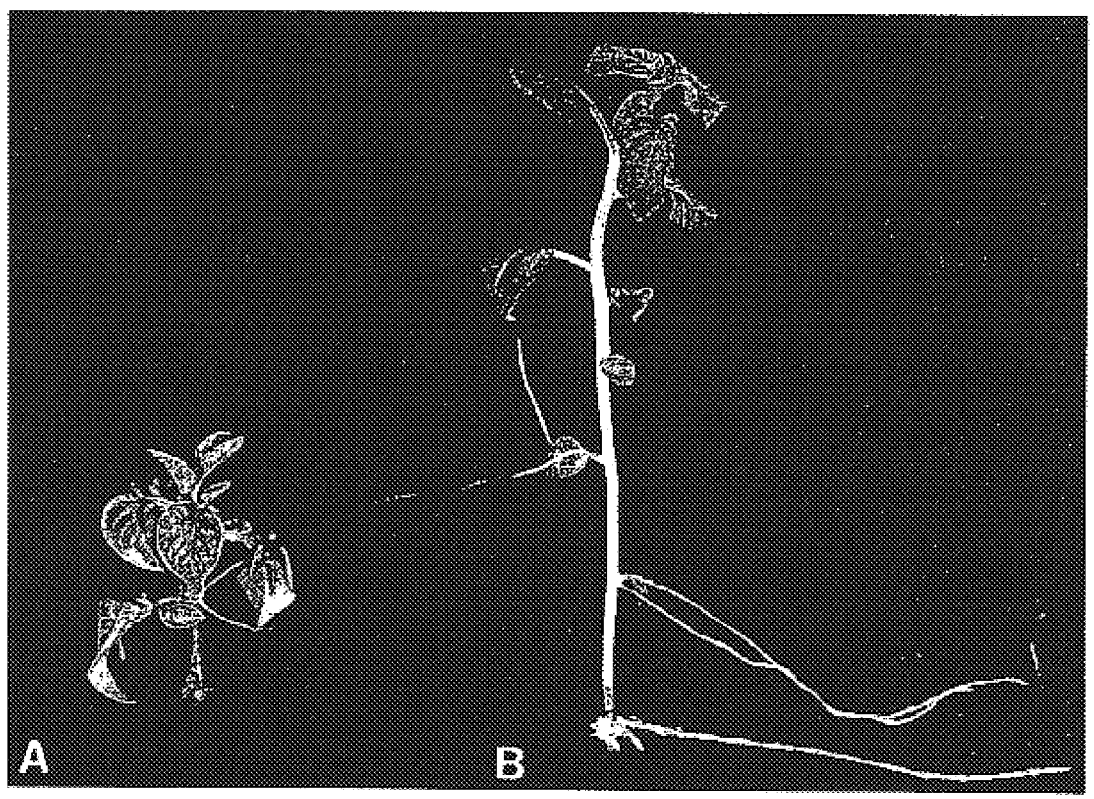

FIG. 8 Detection of the DOG$^R$1 gene mediated resistance in shoots of transgenic potato plants.

Shoots of potato plants *Solanum tuberosum* var. *Solara* were placed on 0.05% 2-DOG containing MS medium. A: five weeks old shoot of an untransformed plant; B: five weeks old shoot of a plant expressing the DOG$^R$1 gene under the control of the 35S promoter.

Figure 9:
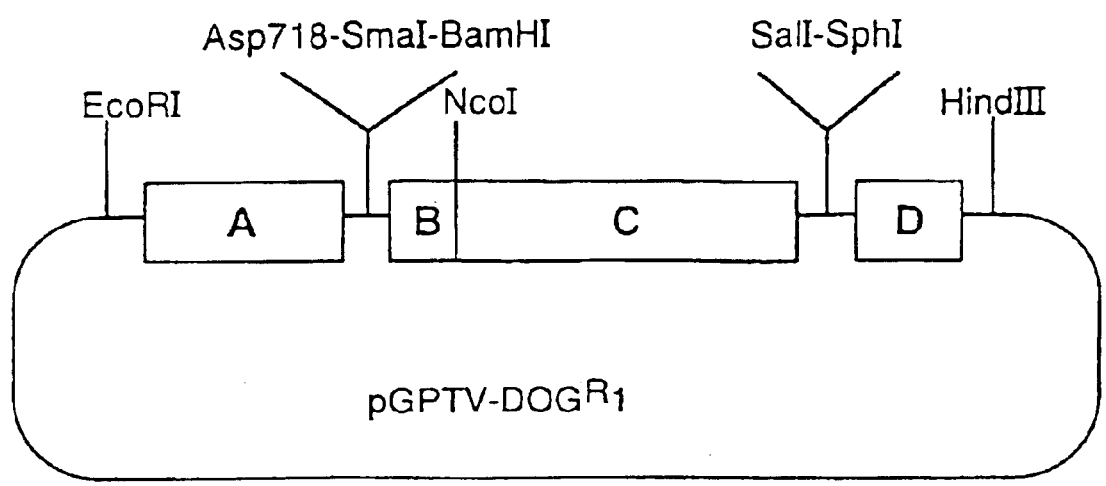

FIG. 9 Plant expression cassette for the over-expression of the DOG$^R$1 gene from yeast (*Saccharomyces cerevisiae* strain 288C) in transgenic pea plants.

Fragment A (529 bp): contains the 35S promoter of the Cauliflower Mosaic Virus (CaMV). It contains a fragment comprising nucleotides 6909 to 7437 of the CaMV.

Fragment B (73 bp): untranslated translation enhancer from Tobacco Mosaic Virus U1 (Gallie (1987) Nucl. Acids Res. 15, 8693).

Fragment C: DOG$^R$1 gene from yeast.

Fragment D (192 bp): contains the polyadenylation signal of gene 3 of the T-DNA of the Ti plasmid pTiACH5.

Fragments A to 4 were cloned into the binary vector pGPTV (Becker (1992) PMB 20, 1195) via EcoRI/HindIII.

Figure 10:
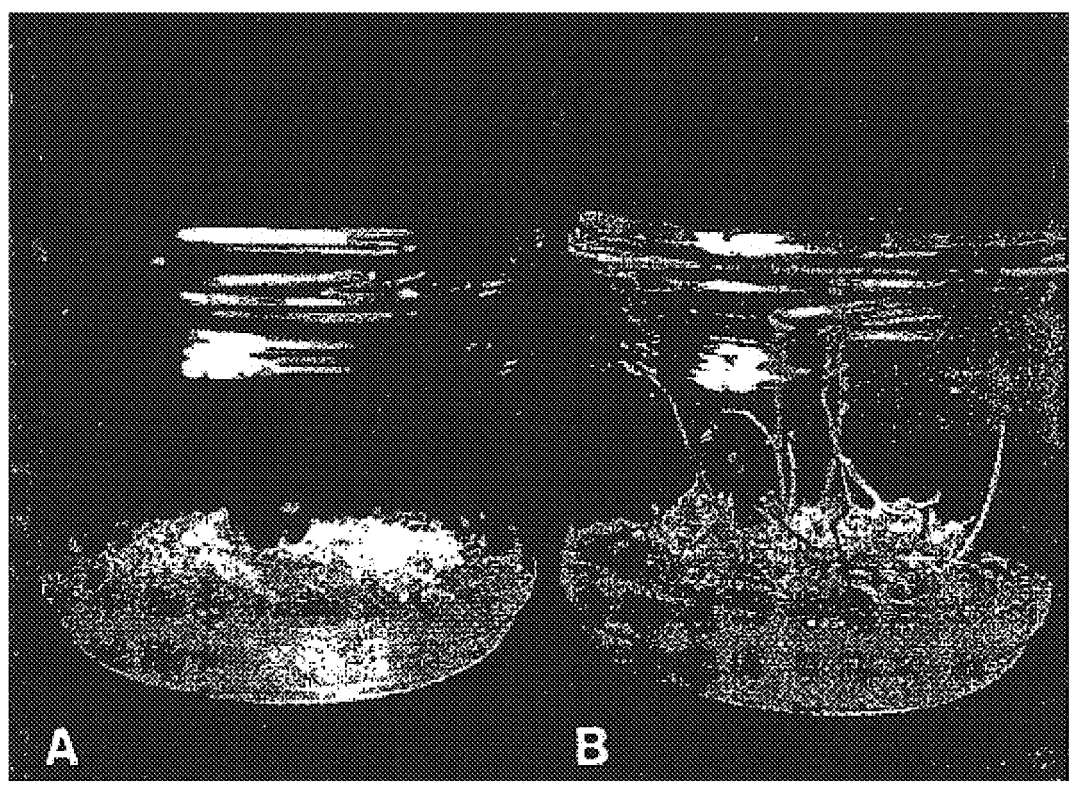

FIG. 10 Detection of the DOG$^R$1 gene mediated resistance in pea plants.

Calli of pea plants *Pisum sativum* were placed on 0.075% 2-DOG containing B5 medium. A: calllus of untransformed plant on 0.075% 2-DOG; B: callus of a plant expressing the DOG$^R$1 gene under the control of the 35S promoter on 0.075% 2-DOG.

DETAILED DESCRIPTION OF THE INVENTION

The problem underlying the present invention is therefore to provide recombinant DNA molecules which contain a DNA sequence useful for the selection of transformed plant cells or plants.

This problem is solved by the provision of the embodiments characterized in the patent claims.

Thus, the present invention relates to a recombinant DNA molecule comprising (a) regulatory sequences of a promoter active in plants;

(b) operably linked thereto a DNA sequence encoding a protein with the biological activity of a 2-deoxyglucose-6-phosphate (2-DOG-6-P) phosphatase; and (c) operably linked thereto regulatory sequences which may serve as transcription termination and/or polyadenylation signals in plants.

In the context of the present invention a protein with the biological activity of a 2-DOG-6-P phosphatase is understood to be a protein which is capable of converting non-metabolizable glucose-analogous compounds such as 2-DOG into non-toxic products. 2-DOG becomes toxic after phosphorylation to 2-DOG-6-P, i.e., the phosphatase offsets the effect of 2-DOG-6-P by dephosphorylation. An alternative resistance mechanism which may also be used within the meaning of the invention is to prevent the phosphorylation or the uptake of 2-DOG. Corresponding mutants are described in yeast, e.g., a transport mutant (Novak (1990) FEBS Lett. 269, 202–204) and a phosphorylation mutant (Lobo (1977) Mol. Gen. Genet. 157, 297–300).

It was surprisingly found that the expression of a 2-DOG-6-P phosphatase from yeast can confer resistance to 2-DOG and can be used to select transformed plants which are otherwise phenotypically normal and fertile. It was known from research done on yeast that the addition of 2-DOG, a non-metabolizable glucose analogue results in the inhibition of the respiration and the growth of cells (Heredia (1964) Biochem. Biophys. Acta 86, 216). In yeast cells the growth inhibition is correlated with a reduced synthesis of structural polysaccharides (Kratky (1975) Eur. J. Biochem. 54, 459) and a blockage of the protein glycosylation (Datema & Schwarz (1978) Eur. J. Biochem. 90, 505), which presumably are caused by changes of the sugar nucleotide concentrations. Beyond the biochemical changes the addition of 2-DOG frequently results in a repression of many genes (summarized in Gancedo (1992) Eur. J. Biochem. 206, 297). In analogy to the mode of action of metabolizable sugars (such as glucose), this process is referred to as catabolite repression.

Figure 1:
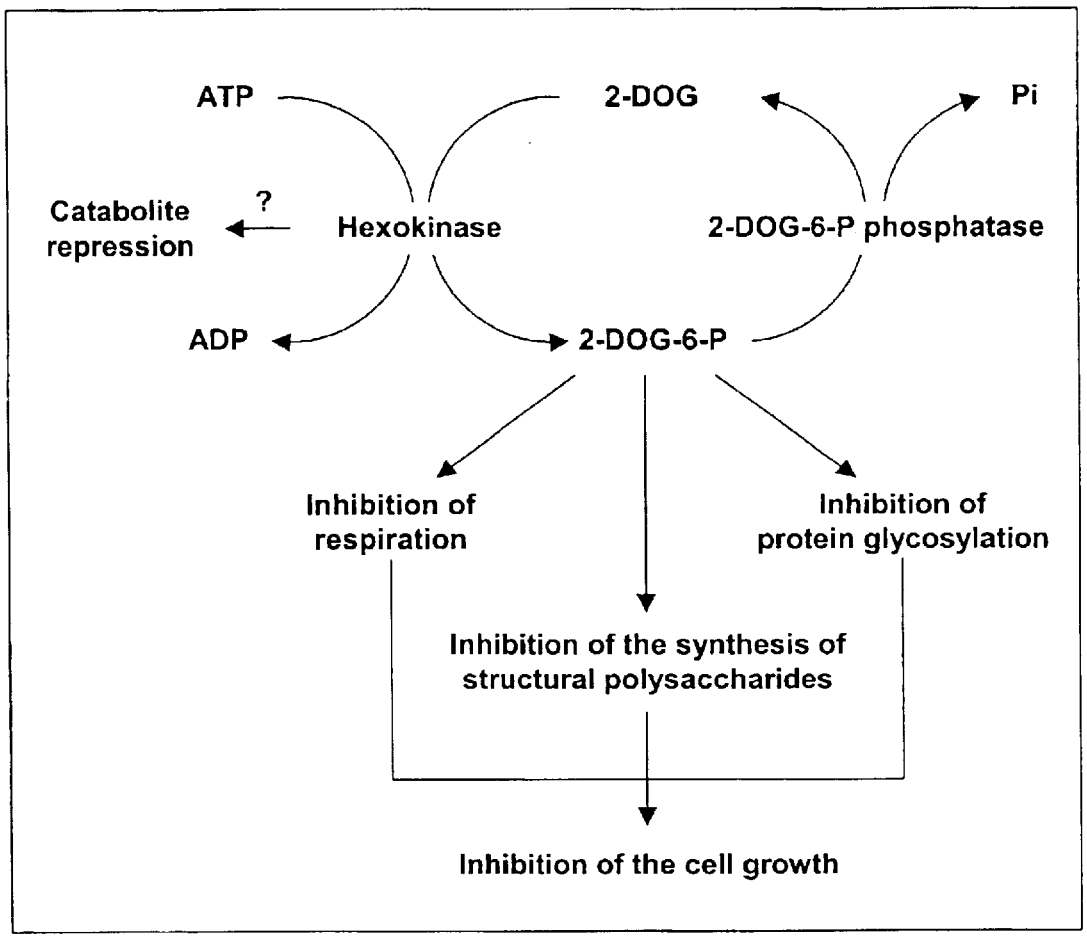
FIG. 1 Possible mechanisms of growth inhibition by 2-deoxyglucose (2-DOG) and removal of the toxic effect by expression of a 2-DOG-6-P phosphatase.

Investigations in yeast cells have shown that the mode of action of 2-DOG depends on the intracellular 2-DOG-6-P concentration. A molecular characterization of yeast mutants which are resistant to 2-DOG showed that the acquired resistance is attributable to the overexpression of a specific 2-DOG-6-P phosphatase (Sanz (1994) Yeast 10, 1195). The hypothetical mode of action and the mode of action of the 2-DOG-6-P phosphatase are shown in FIG. 1.

In contrast to the numerous papers on the mode of action of 2-DOG in animal tissues, in yeasts and in bacteria there are only few analogous studies relating to the metabolism of these sugars in plants. So far it could merely be shown in some studies that the addition of 2-DOG inhibits the root growth of many plants (inter alia flax, vetch, clover, rye, barley, maize and oats (Stenlid (1959) Physiol. Plant. 12, 218; Farrar (1995) J. Exp. Bot. 46, 1859)). Also, the growth of *Nicotiana tabacum* cells and *Picea excelsa* (spruce) cells in tissue culture is strongly inhibited by 2-DOG (Zemek (1975) Z. Pflanzenphysiol. 76, 114; Zemek (1976) Z. Pflanzenphysiol. 77, 95). As reaction products of 2-DOG in higher plants 2-DOG-1-P, 2-DOG-6-P, UDP-2-DOG as well as 2-DOG containing di- and oligosaccharides could be detected (Kocourek (1963) Biochem. Biophys. Acta 71, 497; Zemek (1975) Z. Pflanzenphysiol. 76, 114). The formation of these metabolites is believed to bring about the inhibitory effect of 2-DOG. For other toxic compounds which are used as selection markers in plant transformation manifold effects on the metabolism of the plant have also been reported. For example, the addition of certain antibiotics frequently results in the regeneration of transgenic plants exhibiting physiological and morphological modifications vis-a-vis the phenotype of the wild-type and/or being sterile.

Although, as has been explained above, 2-DOG evokes a number of partly as yet unknown biochemical changes in the cells, phenotypically normal and fertile transgenic plants are regenerated when the recombinant DNA molecules according to the invention are used in combination with the selection on 2-DOG containing media.

The DNA sequence encoding a protein with the biological activity of a 2-DOG-6-P phosphatase can be isolated from natural sources, preferably yeast, or can be synthesized according to known methods.

By using conventional molecular-biological techniques it is possible (see, e.g., Sambrook, 1989, Molecular Cloning, A Laboratory Manual, $2^{nd}$ ed., Cold Spring Harbor Laboratory Press, Cold Spring Harbor, N.Y.) to introduce various mutations into the DNA sequence encoding a protein with the biological activity of a 2-DOG-6-P phosphatase in the recombinant DNA molecules according to the invention, resulting in the synthesis of proteins with biological properties that are possibly modified. First, it is possible to produce deletion mutants in which the synthesis of correspondingly truncated proteins can be achieved by way of progressive deletions at the 5' or the 3' terminus of the coding DNA sequence. Second, it is possible to specifically produce enzymes that are localized in certain compartments of the plant cells due to the addition of corresponding signal sequences. Such sequences are known (see, e.g., Braun, EMBO J. 11 (1992), 3219–3227; Wolter, Proc. Natl. Acad. Sci. USA 85 (1988), 846–850; Sonnewald, Plant J. 1 (1991), 95–106).

Also, the introduction of point mutations at positions is conceivable in which a charge in the amino acid sequence may have an influence on, e.g., the enzyme activity or the regulation of the enzyme. In this way, e.g., mutants with a modified $K_m$ value may be produced, or mutants which are no longer subject to the regulatory mechanisms by allosteric regulation or covalent modification usually occurring in cells.

For the genetic manipulation in prokaryotic cells the recombinant DNA molecules according to the invention or parts of these molecules may be integrated into plasmids which allow for a mutagenesis or a sequence modification by recombination of DNA sequences. By means of standard methods (cf. Sambrook, 1989, Molecular Cloning: A Laboratory Manual, $2^{nd}$ edition, Cold Spring Harbor Laboratory Press, N.Y., USA) base exchanges may be carried out or natural or synthetic sequences may be added. In order to interlink the DNA fragments, adapters or linkers may be attached to the fragments. Moreover, use can be made of manipulations which offer suitable restriction sites or which remove superfluous DNA or restriction sites. Wherever use is made of inserts, deletions or substitutions, in vitro mutagenesis, "primer repair", restriction or ligation may be used. For the purpose of analysis use is usually made of a sequence analysis, a restriction analysis or further biochemico-molecular-biological methods.

In a preferred embodiment the DNA sequence encoding a protein with the biological activity of a 2-DOG-6-P phosphatase is selected from the group consisting of (a) DNA sequences comprising a nucleotide sequence encoding the amino acid sequence indicated in SEQ ID NO. 2;

(b) DNA sequences comprising the nucleotide sequence indicated in SEQ ID NO. 1;

(c) DNA sequences comprising a nucleotide sequence hybridizing to a strand complementary to the nucleotide sequence of (a) or (b);

(d) DNA sequences comprising a nucleotide sequence which is degenerate to the nucleotide sequence of (c); and (e) DNA sequences being a derivative, analogue or fragment of any nucleotide sequence of (a), (b), (c) or (d) and encoding a protein having 2-DOG-6-P phosphatase activity.

In the context of the present invention the term "hybridization" signifies hybridization under conventional hybridization conditions, preferably under stringent conditions as described for example in Sambrook (Molecular Cloning, A Laboratory Manual, 2nd ed. (1989) Cold Spring Harbor Laboratory Press, Cold Spring Harbor, N.Y.).

DNA sequences hybridizing to the DNA sequences encoding a protein with the biological activity of a 2-DOG-6-P phosphatase can be isolated from, e.g., genomic or cDNA libraries prepared from yeast. Such DNA sequences may be identified and isolated, e.g., by hybridization according to standard techniques (see, e.g., Sambrook, 1989, Molecular Cloning, A Laboratory Manual, 2nd ed., Cold Spring Harbor Laboratory Press, Cold Spring Harbor, N.Y.) using, e.g., the DNA sequences which have exactly or substantially the nucleotide sequence indicated under SEQ ID NO. 1 or parts of these sequences, or the reverse complements of these DNA sequences. The fragments used as hybridization probes may also be synthetic fragments which were prepared according to conventional synthesis techniques and the sequence of which is substantially the same as that shown in SEQ ID NO. 2. The DNA sequences encoding a protein with the biological activity of a 2-DOG-6-P phosphatase include DNA sequences the nucleotide sequences of which are degenerate to one of the above-described DNA sequences. The degeneracy of the genetic code allows the skilled person inter alia the possibility of adapting the nucleotide sequence of the DNA sequence to the codon preference of the respective host, preferably plants.

The DNA sequences described above include also fragments, derivative and allelic variants of the DNA sequences described above encoding a protein with the biological activity of a 2-DOG-6-P phosphatase. "Fragments" are understood to be parts of the DNA sequence long enough to encode one of the described proteins. The term "derivative" means in this context that the sequences differ from the above-described DNA sequences in one or more positions but are highly homologous to said sequences. Homology is understood to refer to a sequence identity of at least 40%, particularly an identity of at least 60%, preferably of more than 80% and still more preferably of more than 90%. The proteins encoded by these DNA sequences have a sequence identity to the amino acid sequence shown in SEQ ID NO. 2 of at least 80%, preferably 85% and still more preferably of more than 90%, 95%, 97% and 99%. The deviations from the DNA sequences described above can be the result of deletion, substitution, insertion, addition or recombination.

The DNA sequences that are homologous to the sequences described above and that are derivatives of said sequences are regularly variations of said sequences which represent modifications having the same biological function. They may be naturally occurring variations, such as sequences of other organisms, or mutations. These mutations may occur naturally or may be achieved by specific mutagenesis. Furthermore, these variations may be synthetically produced sequences. The allelic variants may be both naturally occurring variants and variants produced synthetically or by recombinant DNA techniques.

The proteins encoded by the various variants of the DNA sequences contained in the recombinant DNA molecules with the biological activity of a 2-DOG-6-P phosphatase share specific common characteristics, such as enzymatic activity, molecular weight, immunological reactivity or conformation, as well as physical properties, such as electrophoretic mobility, chromatographic behavior, sedimentation coefficients, solubility, spectroscopic properties, stability, pH optimum, temperature optimum.

In a particularly preferred aspect the described DNA sequence is derived from yeast.

In order to express the DNA sequence contained in the recombinant DNA molecules in plant cells, it is linked to regulatory sequences which ensure the transcription in plant cells. Such regulatory sequences are particularly promoters. Basically, any promoter active in plant cells is useful for expression.

The promoter may be selected in such a way that the expression takes place constitutively or in a certain tissue, at a certain point of time of the plant development or at a point of time determined by external circumstances. With respect to the plant the promoter may be homologous or heterologous. Suitable promoters for a constitutive expression are, e.g., the 35S RNA promoter of the Cauliflower Mosaic Virus and the ubiquitin promoter from maize, particularly preferred a promoter ensuring an expression only in photosynthetically active tissues, e.g., the ST-LS1 promoter (Stockhaus, Proc. Natl. Acad. Sci. USA 84 (1987), 7943–7947; Stockhaus, EMBO J. 8 (1989), 2445–2451) or a promoter which is active during plant transformation, plant regeneration or certain stages of these processes, e.g., cell-division specific promoters such as the Histon H-3 promoter (Kapros (1993), In Vitro Cell Dev. Biol. Plant 29, 27–32) or the chemically inducible Tet system (Gatz (1991), Mol. Gen. Genet. 227, 229–237). An overview of further possible promoters can be found, e.g., in Ward (1993) Plant Mol. Biol. 22, 361–366.

Also preferred are inducible or cell-specific promoters (e.g., meristem).

Furthermore, a transcription termination sequence may exist which serves to correctly end the transcription and to add a poly-A tail to the transcript which is believed to stabilize the transcripts. Such elements, e.g., the terminator of the octopin synthase gene from Agrobacteria, are described in the literature (cf. Gielen, EMBO J. 8 (1989), 23–29) and can be exchanged as desired.

In a preferred embodiment the promoter is the 35S CAMV promoter.

The invention furthermore relates to vectors containing the recombinant DNA molecules according to the invention. Preferably, these vectors are plasmids, cosmids, viruses, bacteriophages and other vectors common in genetic engineering. For the preparation of the introduction of foreign genes into taxonomically higher plants there is a wide choice of cloning vectors that contain a replication signal for *E. coli* and a marker gene for the selection of transformed bacterial cells. Examples of such vectors are pBR322, pUC series, M13mp series, pACYC184, etc. The desired sequence can be introduced into the vector at a suitable restriction site. The plasmid obtained is used to transform *E. coli* cells. Transformed *E. coli* cells are cultivated in a suitable medium, harvested and lysed. The plasmid is recovered. As methods for the analysis for the characterization of the obtained plasmid DNA restriction analyses, gel electrophoreses and other biochemical molecular-biological methods are generally used. After each manipulation the plasmid DNA can be cleaved and the resulting DNA fragments can be linked to other DNA sequences. Any plasmid DNA sequence can be cloned into the same or other plasmids.

In a preferred embodiment the vector according to the invention contains at least one further recombinant DNA molecule. The provision of the DNA molecules and vectors according to the invention allows the transfer of any information contained in another recombinant DNA molecule to plants or plant cells and the selection of the desired information by selection on 2-DOG containing media. Naturally, the person skilled in the art knows that the recombinant DNA molecule containing the additional information does not necessarily have to be present in the vector carrying the selection marker but can also be co-transformed with it (Lyznik (1989) Plant Mol. Biol. 13, 151–161; Peng (1995) Plant Mol. Biol. 27, 91–104). This is an option if no physical coupling of the marker gene and the information to be transferred is desired. In this case, the marker gene and the desired information can segregate independently of each other in the subsequent cross-breedings after selection of the primary transgenic plant.

In a particularly preferred embodiment the other recombinant DNA molecule contains a DNA sequence encoding a peptide, protein, anti-sense or sense RNA, viral RNA, or a ribozyme. Some examples of heterologous (over)expression and of anti-sense inhibition with the purpose of manipulating the metabolic flow in transgenic plants are summarized in Herbers & Sonnewald (1996) TIBTECH 14, 198–205. An example for ribozymes was published by Feyter (1996) Mol. Gen. Genet. 250, 329–338. By expressing a "hammerhead" ribozyme the authors succeeded in producing a TMV resistance in transgenic tobacco plants. Various possible applications of transgenic plants which can be produced using the recombinant DNA molecules and vectors according to the invention are described in TIPTEC Plant Product & Crop Biotechnology, 13 (1995), 312–397.

The vectors according to the invention may possess further functional units stabilizing the vector in the host organism such as a bacterial replication origin or the 2-micron DNA for the stabilization in *Saccharomyces cerevisiae*. Also, "left border" and "right border" sequences of agrobacterial T-DNA may be present allowing a stable integration into the genome of plants. Another strategy of producing marker-free transgenic plants is to use sequence-specific recombinases. For this purpose, e.g., two strategies are possible: (i) re-transformation of a recombinase-expressing starting line and out-crossing of the recombinase after removal of the selection marker which was associated with the desired gene; (ii) co-transformation with subsequent out-crossing. The prerequisites for this recombinase strategy are (i) flanking of the selection marker with recognition sequences for the recombinase and (ii) a recombinase which is active in plants and does not use the plant's own sequences for recombination. Such processes are available in the art to the skilled person, e.g., RecA (Reiss (1996) Proc. Natl. Acad. Sci. USA 93, 3094–3098), Cre/lox (Bayley (1992) Plant Mol. Biol. 18, 353–361), FLP/FRT (Lloyd (1994) Mol. Gen. Genet. 242, 653–657), Gin (Maeser (1991) Mol. Gen. Genet. 230, 170–176) and R/RS (Onouchi (1991) Nucl. Acids Res. 19, 6373–6378).

In another embodiment the invention relates to host cells which transiently or stably contain the recombinant DNA molecules or vectors according to the invention. A host cell is understood to be an organism which is capable of taking up DNA which was recombined in vitro and optionally of expressing the DNA sequence contained in the recombinant DNA molecule according to the invention.

Preferably, these cells are prokaryotic or eukaryotic cells. Particularly, the invention relates to plant cells containing the vector systems according to the invention or derivatives or parts thereof. The cells—due to the uptake of the vector systems according to the invention or derivatives or parts thereof—preferably are capable of synthesizing enzymes possessing the biological activity of a 2-DOG-6-P phosphatase. Preferably, the cells according to the invention are characterized in that the introduced recombinant DNA molecule according to the invention is either heterologous with respect to the transformed cell, i.e., it does not naturally occur in these cells, or is localized in a different locus in the genome than the corresponding naturally occurring sequence.

In a further embodiment the invention relates to kits containing a recombinant DNA molecule according to the invention or a vector according to the invention and optionally 2-DOG or a chemical compound equivalent to 2-DOG. For example, Schmidt (1978) (Eur. J. Biochem. 87, 55–68) described 2-deoxy-2-fluoro-D-glucose or mannose as labeled analogues.

The provision of the recombinant DNA molecules and vectors according to the invention allows the use of 2-DOG as selection medium for plant transformation, preferably for the selection of transformed plants derived from high yield varieties for which the state of the art selection markers frequently are of only restricted usefulness.

The present invention thus also relates to a process for selecting transformed plant cells comprising the following steps:

(a) obtaining plant cells;
(b) introducing a recombinant DNA molecule or vector according to the invention into these plant cells; and
(c) selecting the successfully transformed plant cells on 2-DOG containing media or on media containing a chemical compound functionally equivalent to 2-DOG.

There is a large number of techniques available for the introduction of DNA into a plant host cell. These techniques include the transformation of plant cells with T-DNA using *Agrobacterium tumefaciens* or *Agrobacterium rhizogenes* as transformant, the fusion of protoplasts, injection, electroporation of DNA, the introduction of DNA via the biolistic technique and other possible techniques.

In the case of injection and electroporation of DNA into plant cells no specific requirements are made to the plasmids used. Simple plasmids such as pUC derivatives can be used. If, however, one intends to regenerate whole plants from the respectively transformed cells, it is necessary that a selectable marker gene be present.

Depending on the method of introduction of the desired genes into the plant cell further DNA sequences can be necessary. If, e.g., the Ti or Ri plasmid is used to transform the plant cell, at least the right border, often, however, the right and left border of the Ti and Ri plasmid T-DNA must be linked as flanking region to the genes to be introduced.

If Agrobacteria are used for transformation, the DNA to be introduced must be cloned into special plasmids, either into an intermediate vector or into a binary vector. The intermediate vectors can be integrated by homologous recombination into the Ti or Ri plasmid of the Agrobacteria due to sequences that are homologous to sequences in the T-DNA. Said plasmid contains the vir region necessary for the transfer of the T-DNA. Intermediate vectors are not capable of replicating in Agrobacteria. The intermediate vector can be transferred to *Agrobacterium tumefaciens* using a helper plasmid (conjugation). Binary vectors are capable of replicating both in *E. coli* and in Agrobacteria. They contain a selection marker gene and a linker or polylinker flanked by the right and left T-DNA border regions. They can be directly transformed into Agrobacteria (Holsters, Mol. Gen. Genet. 163 (1978), 181–187). The Agrobacterium serving as host cell should contain a plasmid carrying a vir region. The vir region is necessary for the transfer of the T-DNA to the plant cell. Additional T-DNA may be present. The Agrobacterium transformed in this manner is used to transform plant cells. Intensive research work was done on the use of T-DNA for the transformation of plant cells and is described in EP-A-120 516; Hoekema: The Binary Plant Vector System, offsetdrukkerij Kanters B. V., Alblasserdam (1985), Chapter V; Fraley, Crit. Rev. Plant. Sci., 4, 1–46 and An, EMBO J. 4 (1985), 277–287.

In a preferred embodiment the vector according to the invention is transferred to plant cells in the process according to the invention using Agrobacterium tumefaciens.

For the transfer of the DNA into the plant cell, it is suitable to co-cultivate plant explants with Agrobacterium tumefaciens or Agrobacterium rhizogenes. From the infected plant material (for example leaf explants, segments of stems, roots but also protoplasts or suspension-cultivated plant cells) whole plants can be regenerated in a suitable medium which contain 2-DOG or a functionally equivalent chemical agent for the selection of transformed cells. The plants obtained that way can then be examined for the presence of the introduced DNA. Other possibilities of introducing foreign DNA using the biolistic method or by protoplast transformation are known (cf. e.g., Christou (1996) Trends in Plant Science 1, 423–431; Willmitzer, L., 1993 Transgenic plants. In: Biotechnology, A Multi-Volume Comprehensive Treatise (H. J. Rehm, G. Reed, A. Puhler, P. Stadler, eds.), Vol. 2, 627–659, VCH Weinheim-New York-Basel-Cambridge).

Alternative systems for the transformation of monocotyledonous plants are the transformation via the biolistic approach, the electrically or chemically induced DNA incorporation into protoplasts, the electroporation of partially permeabilized cells, the macroinjection of DNA into inflorescences, the microinjection of DNA into microspores and pro-embryos, the DNA integration by germinating pollen and the DNA integration into embryos by swelling (for an overview see Potrykus, Physiol. Plant (1990), 269–273).

While the transformation of dicotyledonous plants via Ti plasmid vector systems using *Agrobacterium tumefaciens* is a well-established method, more recent research has shown that monocotyledonous plants, too, may very well be transformed by way of Agrobacteria-based vectors (Chan, Plant Mol. Biol. 22 (1993), 491–506; Hiei, Plant J. 6 (1994), 271–282; Bytebier, Proc. Natl. Acad. Sci. USA 84 (1987), 5345–5349; Raineri, Bio/Technology 8 (1990), 33–38; Gould, Plant Physiol. 95 (1991), 426–434; Mooney, Plant, Cell Tiss. & Org. Cult. 25 (1991), 209–218; Li, Plant Mol. Biol. 20 (1992), 1037–1048).

Three of the above-mentioned transformation systems could be established in the past for various cereals: the electroporation of tissue, the transformation of protoplasts and the DNA transfer by particle bombardment in regenerative tissues and cells (for an overview: Jähne, Euphytica 85 (1995), 35–44). The transformation of wheat is frequently described in the literature (for an overview: Maheshwari, Critical Reviews in Plant Science 14 (2) (1995), 149–178).

In another preferred embodiment the recombinant DNA molecule according to the invention or the vector according to the invention is transferred in the process according to the invention by particle bombardment (biolistic method).

The present invention also relates to transgenic plant cells containing a recombinant DNA molecule according to the invention or a vector according to the invention or were obtained by the process according to the invention as well as transgenic plant cells derived from such transformed plant cells. Such cells can be distinguished from naturally occurring plant cells in that they contain at least one recombinant DNA molecule according to the invention which does not naturally occur in these cells or in that such a molecule is integrated in a locus in the genome other than the corresponding naturally occurring molecule, i.e., in a different genomic surrounding.

In a preferred embodiment the plant cell according to the invention contains at least one other foreign gene. As already mentioned in the introduction of the present application the possibility of controlling complex metabolic processes requires the manipulation of several enzymatic steps and the ability of the transgenic plants to undergo multiple transformations is therefore essential. By use of the recombinant DNA molecules and vectors according to the invention the skilled person can now rely on new markers for the selection of plant cells which were subjected to multiple transformations.

The transgenic plant cells can be regenerated to whole plants according to techniques known to the person skilled in the art. The plants obtainable by regeneration of the transgenic plant cells according to the invention are also a subject matter of the invention. Another subject matter of the invention are plants and plant tissues containing the above-described transgenic plant cells. Depending on the promoter chosen (e.g., 35S CaMV) the adult plants, too, are resistant to 2-DOG and may be selected for by adding this compound. When using, e.g., tissue-specific promoters this is not possible and the person skilled in the art may rely on, e.g., molecular-biological methods such as PCR in order to identify these plants. Those skilled in the art may also place seed of such plants on 2-DOG containing media after, e.g., self-fertilization or back-crossing against the parent, and may draw conclusions from the germination capacity of these seeds or the survival of the plants at a later stage of development (depending on the promoter chosen) whether the plants are transgenic or not. The transgenic plants may generally be plants of any plant species, i.e., both monocotyledonous and dicotyledonous plants. Preferably, the plants are useful plants such as wheat, barley, rice, rape, pea, maize, sugar beet, sugar cane or potato.

The invention also relates to the propagation material and harvest products of the plants according to the invention, for example, fruits, seeds, tubers, root stocks, seedlings, cuttings, etc.

As already explained above, the present invention provides recombinant DNA molecules and vectors which are suitable as selection markers in plant cells for the selection of transformed plant cells as well as transgenic plants, plant cells and/or tissues according to the invention derived therefrom. Thus, the present invention also relates to the use of a recombinant DNA molecule according to the invention or a vector according to the invention for the production of transgenic plants, plant cells and/or tissues as well as their use as selectable markers in plant cell and tissue culture and/or plant breeding.

The Methods Used in the Examples

1. General Cloning Methods

Cloning methods such as: restriction cleavage, DNA isolation, agarose gel electrophoresis, purification of DNA fragments, transfer of nucleic acids on nitrocellulose and nylon membranes, linking of DNA fragments, transformation of E. coli cells, culturing bacteria, sequence analysis of recombinant DNA were carried out as described in Sambrook (Cold Spring Harbor Laboratory Press (1989); ISBN 0-87969-309-6). *Agrobacterium tumefaciens* was transformed according to the method described by Höfgen and Willmitzer (Nucl. Acid Res. (1988) 16, 9877). The Agrobacteria were grown in YEB medium (Vervliet, Gen. Virol. (1975) 26, 33).

2. Bacterial Strains

E. coli (XL-1 Blue) bacteria were obtained from Stratagene. The Agrobacterium strain (C58C1 with the plasmid pGV 3850kan) used for plant transformation was described by Deblaere (1985, Nucl. Acid Res. 13, 4777).

3. Analysis of Whole RNA from Plant Tissues

Plant whole RNA was isolated according to the method by Logemann (1987, Analytical Biochem. 163, 16) and separated on formaldehyde agarqae gels (Lehrach (1977) Biochem. 16, 4743). A capillary transfer on nylon membranes (Gene Screen, NEN) was carried out in 20×SSC (1.5 M NaCl, 150 mM sodium citrate) overnight. After pre-hybridization for two hours in hybridization buffer (500 mM sodium phosphate (pH 7.2), 7% SDS, 1% bovine serum albumin, 200 µg herring sperm DNA, 1 mM EDTA), the hybridization was carried out at 55° C. for 16 hours with the radioactively labeled $DOG^R1$ probe. As probe the $DOG^R1$ coding region was isolated from plasmid pGEMT and radioactively labeled in the presence of $\alpha$-$^{32}$P-dCTP using a High Prime Kit (Boehringer). Then, the filters were washed under the following conditions: 20 minutes at 55° C. in 6×SSC, 0.1% SDS and 20 minutes at 55° C. in 4×SSC, 0.1% SDS.

4. Detection of DOG-6-P in Plant Extracts

For the detection of the 2-DOG-6-P phosphatase activity in the transgenic plants leaf disks (about 100 mg fresh weight) were incubated in 300 mM 2-DOG solution for 24 hours in the dark. Then the leaf disks were washed with water for 1 minute and frozen in liquid nitrogen. For an extraction of the metabolites the plant material was homogenized to a fine powder in a mortar which had been pre-cooled on dried ice and mixed with 1.5 ml 16% (w/v) trichloroacetic acid (TCA) in diethylether (pre-cooled to 40° C.). Then the homogenates were incubated on dried ice for 15 minutes. The metabolites were dissolved by adding 0.8 ml 16% TCA (w/v), 5 mM EGTA. After the homogenates were transferred to Eppendorf reaction vials they were incubated at 4° C. for 3 hours. The samples were then centrifuged at 15,000 rpm at 4° C. for 5 minutes in a Biofuge 15R (Heraeus). The aqueous phase was transferred to Eppendorf reaction vials and washed four times with ether which was saturated with water. The samples were then neutralized with 5 M KOH/1 M triethanolamine mixture and gassed with nitrogen for 1 minute. The samples prepared in such a manner were analyzed by HPLC. For the analysis a HPLC system of Dionex was used which was equipped with a PA-1 (4×250 mm) column and a pulsed electrochemical detector. Prior to the injection the samples were centrifuged at 13,000 rpm for 2 minutes. Metabolites were then eluted with a 50 minute concave gradient (curve 9) of 1 mM to 500 mM sodium acetate after 40 minutes at 10 mM NaOH and a flow rate of 1 ml/min. Isocratic elution was carried out for another 5 minutes. For the identification and quantification of 2-DOG-6-P, 2-DOG-6-P of Sigma was used as standard.

The Examples Serve to Illustrate the Invention

EXAMPLE 1

Detection of the Toxicity of 2-deoxyglucose (2-DOG) for Plant Cells

Figure 2A:
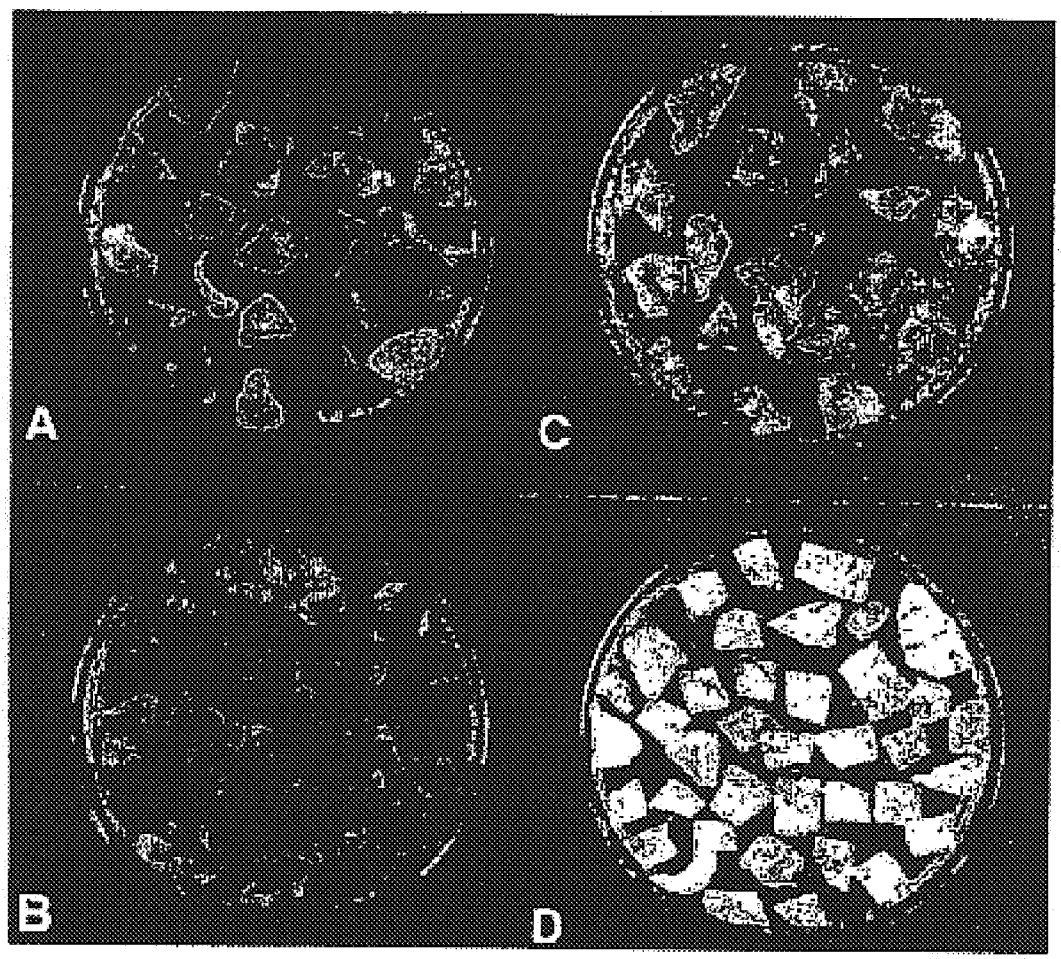
FIGS. 2A and 2B Cultivation of tobacco (Nicotiana tabacum Var. Samsun NN, A-D) and potato (Solanum tuberosum var. Solara, E-H) leaf disks on 2-DOG-containing MS medium. A, E: control MS medium without addition of 2-deoxyglucose; B, F: MS medium with 0.05% 2-DOG; C, G:MS medium with 0.1% 2-DOG; D, H: MS medium with 0.5% 2-DOG.
Figure 2B:
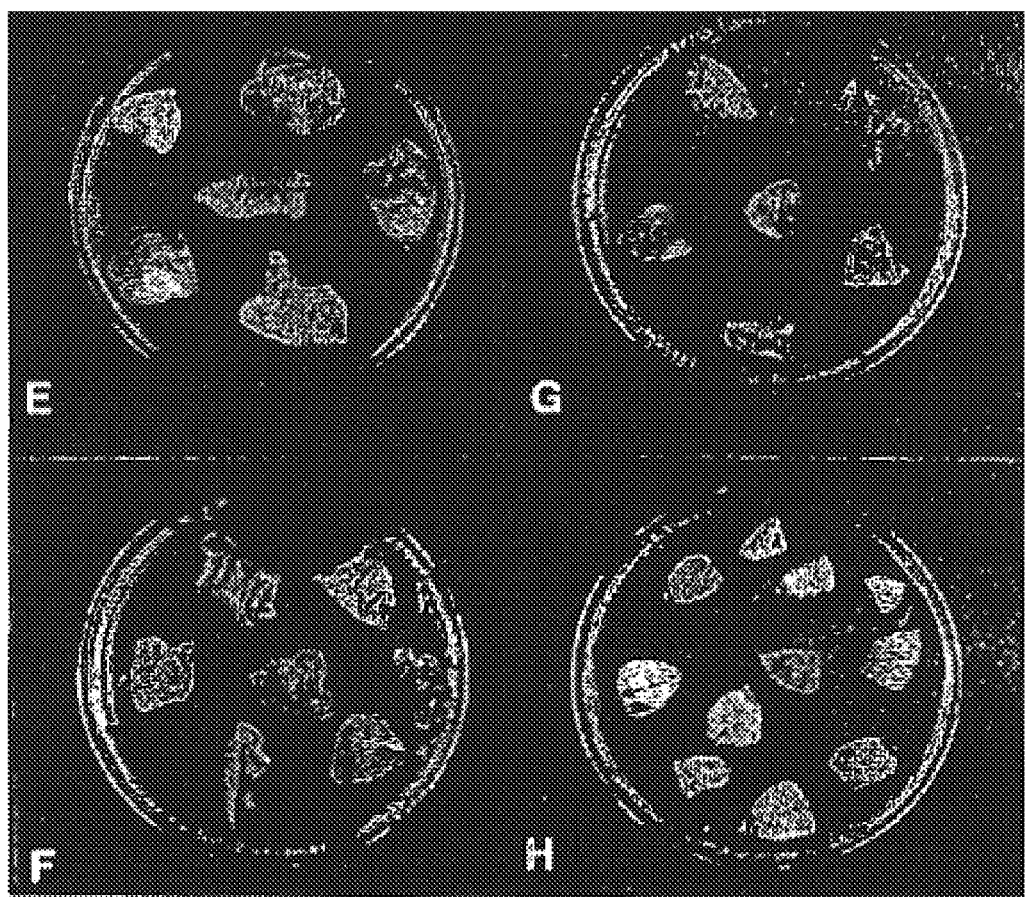
Figure 2C:
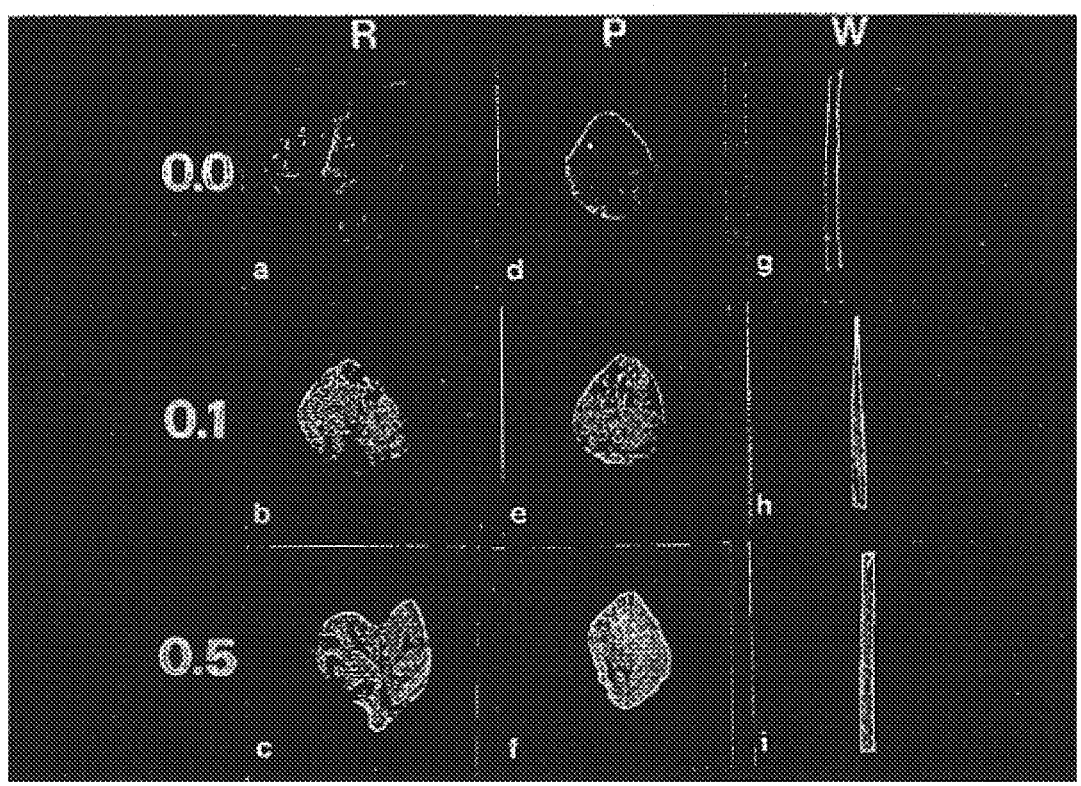
FIG. 2C Cultivation of pea, rape and wheat leaf disks on 2-DOG containing MS medium. R, rape; P, pea; W, wheat. 0.0, 0.1 and 0.5: added 2-DOG concentration in %.

For the detection of the toxicity of 2-DOG leaf pieces (about 1 cm²) of sterile tobacco and potato plants were cultivated for two weeks on Murashige and Skoog medium (Murashige & Skoog (1962) Physiol. Plant. 15, 473), to which 0.01 to 0.5% 2-DOG had been added. As shown in FIG. 2, the addition of 2-DOG (FIG. 2, B-D and F-H) caused the leaf disks to die.

EXAMPLE 2

Figure 3:
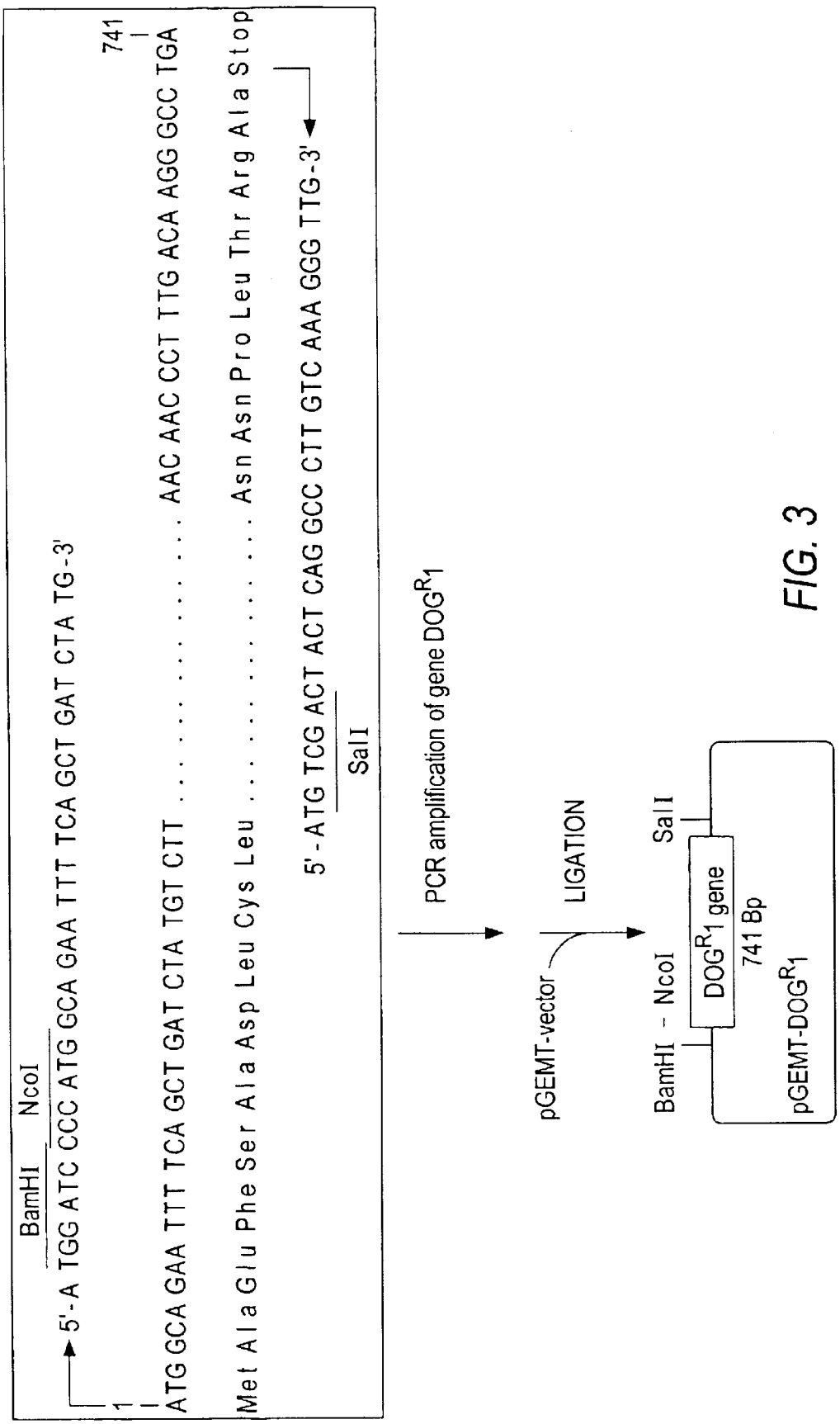
FIG. 3 Schematic representation of the PCR amplification of the 2-DOG-6-P phosphatase from Saccharomyces cerevisiae strain 288C.

PCR Amplification of the 2-DOG-6-P Phosphatase from Saccharomyces Cerevisiae Strain S288C The $DOG^R1$ coding region was cloned by Polymerase Chain Reaction (PCR). The matrix material used was genomnic yeast DNA which was isolated from *Saccharomyces cerevisiae* strain S288C according to standard protocol. Amplification was carried out using the specific primers $DOG^R1-1$ (5'-ATGGATCCCCATGGCAGAATTTTCAG-CTGATCTATG-3'; SEQ ID NO:3) and $DOG^R1-2$ (5' ATGTCGACTACTCAGGCCCTTGTCAAAGGGTTG-3'; SEQ ID NO:4), which were derived from a published sequence (Sanz (1994) Yeast 10, 1195–1202). Primer 1 includes bases 1 to 26 and primer 2 bases 720 to 741 of the coding region of the $DOG^R1$ gene. For the cloning of the amplified DNA into plant expression vectors the primers additionally carry the following restriction sites: primer 1, BamHI and NcoI; primer 2, SalI. The cloning strategy is depicted in FIG. 3. The PCR ow reaction mixture (50 μl) contained chromosomal yeast DNA (1 μg), primers 1 and 2 (1 μg each), 10 mM Tris-HCl (pH 8.8 at 25° C.), 3.5 mM $MgCl_2$, 50 mM KCl, 0.1% Triton X-100, 200 μM dNTPs (dATP, dCTP, dGTP, dTTP) and 2 units PrimeZyme DNA Polymerase (Biometra). Before the polymerase was added the mixture was heated to 94° C. for 10 minutes. The polymerization steps (60 cycles) were carried out in an automated "Thermocycler" (Perkin Elmer) according to the following program: denaturation at 94° C. (1 minute), annealing of the primers at 40° C. (1 minute), polymerase reaction at 72° C. (1 minute). The fragment obtained was cloned into the vector pGEMT (Promega Corp., 2800 Woods Hollow Road, Madison, Wis. 53711–5399, USA) and the plasmid pGEMT-$DOG^R1$ was obtained. The identity of the amplified DNA was verified by sequence analysis.

EXAMPLE 3

Preparation of Plasmid p35S- $DOG^R1$

Figure 4:
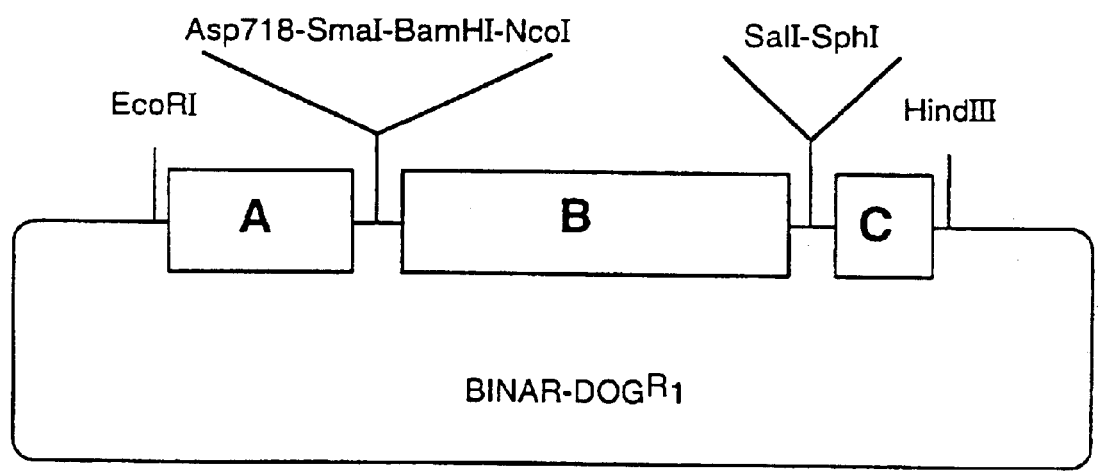
FIG. 4 Plant expression cassette for the overexpression of the $DOG^R1$ gene from yeast (Saccharomyces cerevisiae strain S288C) in transgenic plants. Fragment A (529 bp): contains the 35S promoter of the Cauliflower Mosaic Virus (CaMV). It contains a fragment including nucleotides 6909 to 7437 of the CaMV. Fragment B: $DOG^R1$ gene from yeast which was isolated as BamHI/SalI fragment from plasmid pGEMT-$DOG^R1$ (cf.

A DNA sequence encoding 2-DOG-6-P phosphatase was isolated from plasmid pGEMT- $DOG^R1$ and provided with the 35S promoter of the Cauliflower Mosaic Virus, which effects a constitutive expression in transgenic plants, as well as with a plant transcription termination signal. The plant transcription termination signal contains the 3' terminus of the polyadenylation site of the octopin synthase gene. The plasmid p35S-$DOG^R1$contains three fragments A, B and C which were cloned into the cleavage sites for restriction enzymes of the polylinker of pUC 18 (cf. FIG. 4).

Fragment A contains the 35S promoter of the Cauliflower Mosaic Virus (CaMV). It contains a fragment which comprises nucleotides 6909 to 7437 of the CaMV (Franck (1980) Cell 21, 285) and was isolated as EcoRI-KpnI fragment from the plasmid pDH51 (Pietrzak (1986) Nucleic. Acid Res. 14, 5857) and cloned between the EcoRI-KpnI cleavage sites of plasmid pUC18.

Fragment B contains the $DOG^R1$ coding region which was isolated as BamHI-SalI fragment from plasmid pGEMT-$DOG^R1$ (see FIG. 3) and cloned between the BamHI-SalI cleavage sites of pUC18.

Fragment C contains the polyadenylation signal of gene 3 of the T-DNA of the Ti-plasmid pTiACH5 (Gielen (1984) EMBO J. 3, 835), which was nucleotides 11749–11939, which was isolated as PvuII-HindIII fragment from plasmid pAGV 40 (Herrera-Estrella (1983) Nature 303, 209) and cloned between the SphI-HindIII cleavage sites of the polylinker of pUC 18 after SphI linker had been added to the PvuII-cleavage site.

The chimeric gene was then cloned as EcoRI-HindIII fragment between the EcoRI-HindIII cleavage sites of the plasmid pBIN19 (Bevan (1984) Nucleic. Acid Res. 12, 8711).

EXAMPLE 4

Selection of $DOG^R1$ Transformed Plant Cells and Plant Regeneration on 2-DOG Containing Medium 10 ml of a selectively grown overnight culture of *Agrobacterium tumefaciens* were centrifuged off, the supernatant was discarded and the bacteria were resuspended in equal volumes of antibiotics-free medium. In a sterile Petri dish leaf disks of sterile *Nicotiana tabacum* Var. *Samsun* NN plants (ca. 1 $cm^2$) from which the middle rib was removed were bathed in this bacterial culture. The leaf disks were then densely plated on Petri dishes containing MS medium comprising 2% sucrose and 0.8% Bacto Agar. After two days' incubation at 25° C. in the dark they were transferred to MS medium containing 0.05% 2-DOG, 400 mg/1 β-Bactyl, 1 mg/1 benzaminopurine (BAP), 0.2 mg/1 naphthyl acetic acid (NAA), 1.6% glucose and 0.8% Bacto Agar. After callus formation the leaf disks were transferred until shoot induction to MS medium containing 0.02% 2-DOG, 400 mg/1 β-Bactyl, 1 mg/1 benzaminopurine (BAP), 0.2 mg/1 naphthyl acetic acid (NAA), 1.6% glucose and 0.8% Bacto Agar. Growing shoots were transferred to hormone-free MS medium with 200 mg/1 β-Bactyl and 2% sucrose for root induction. Radicate shoots were then transferred to soil culture and were cultivated in a greenhouse.

EXAMPLE 5

Detection of the Chimeric $DOG^R1$ Gene in the Transformed Plants by PCR

Figure 5:
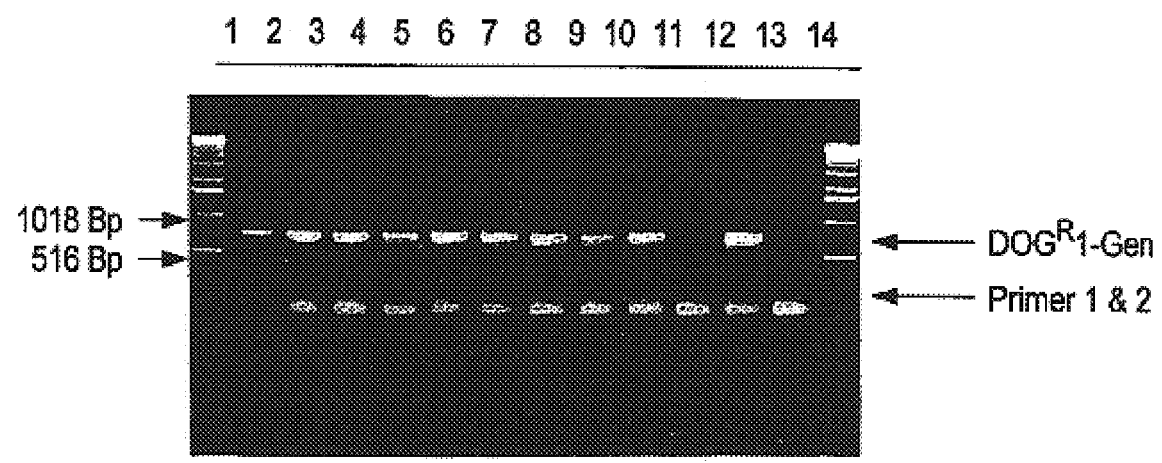
FIG. 5 Detection of the $DOG^R1$ gene by PCR amplification in genomic DNA of the transgenic tobacco plants. Lanes 1 and 14, DNA length standard; lanes 2–10, independent transformants; lane 11, untransformed control plant; lane 12, positive control (plasmid pGEMT-$DOG^R1$); lane 13, water control.

For the detection of a successful transformation genomic DNA of the transgenic tobacco plants was isolated according to the method by Rogers and Bendich (Plant Mol. Biol. (1985) 5, 69) and the chimeric $DOG^R1$ gene was detected by PCR amplification. The PCR reaction mixture (50p1) contained genomic tobacco DNA (1 μg), primers 1 and 2 (1 μg each), 10 mM Tris-HCl (pH 8.8 at 25° C.), 3.5 mM $MgCl_2$, 50 mM KCl, 0.1% Triton X-100, 200 μM dNTPs (DATP, dCTP, dGTP, dTTP) and 2 units PrimeZyme DNA polymerase (Biometra). Before the polymerase was added the mixture was heated to 94° C. for 10 minutes. The polymerization steps (40 cycles) were carried out in an automated "Thermocycler" (Perkin Elmer) according to the following program: denaturation at 94° C. (1 minute), annealing of the primers at 40° C. (1 minute), polymerase reaction 72° C. (1 minute). Then an aliquot of the PCR reaction was separated on an agarose gel. As shown in FIG. 5, an about 740 base-pair long DNA fragment is amplified using genomic DNA of transgenic plants as matrix which fragment is not detectable when genomic DNA of untransformed control plants is used.

EXAMPLE 6

Figure 6:
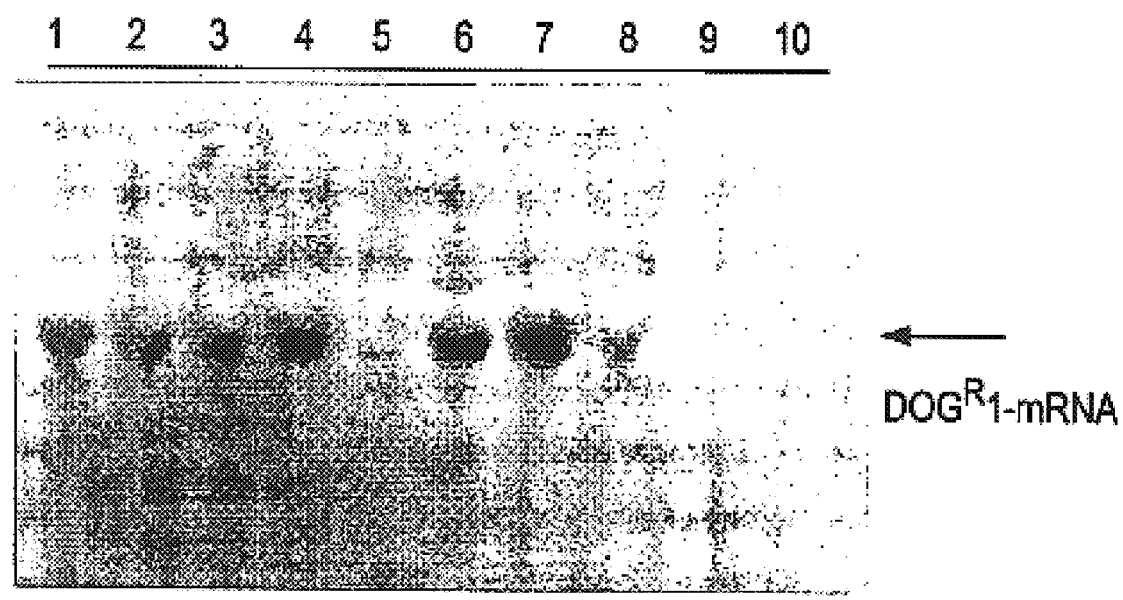
FIG. 6 Detection of the expression of the chimeric DOG$^R$1 gene in 2-DOG resistant tobacco plants by RNA analysis.

Detection of the Expression of the Chimeric $DOG^R1$ Gene in 2-DOG-resistant Tobacco Plants by RNA Analysis The expression of the 2-DOG-6-P phosphatase in the regenerated plants was verified by RNA analyses. For this purpose, leaf samples of the plants transferred to the greenhouse were harvested, whole RNA was extracted, separated by electrophoresis, transferred to nylon membranes and hybridized to the coding region of the $DOG^R1$ gene. As shown in FIG. 6, the 2-DOG-6-P phosphatase mRNA could be detected in the tobacco plants which had been regenerated on 2-DOG. A cross-reaction with untransformed tobacco plants was not observed.

EXAMPLE 7

In vivo Detection of the 2-DOG-6-P Phosphatase Activity

The in vivo activity of the 2-DOG-6-P phosphatase was detected as follows: 0.78 cm² leaf disks of untransformed tobacco plants and the transformants 35S-DOG-3, 4, 8, 9 and 11 were incubated in a 300 mM 2-DOG solution in the dark for 24 hours. For the detection of the 2-DOG-6-P produced the phosphorylated intermediates were isolated and separated by HPLC. As shown in Table 1, the expression of the 2-DOG-6-P phosphatase results in a decrease in 2-DOG-6-P accumulation.

TABLE 1

Detection of 2-DOG-6-P in leaf disks of transgenic and untransformed tobacco plants

| Genotype | [$\mu$mol m$^{-2}$] 2-DOG-6-P | [% of the control] 2-DOG-6-P |
|---|---|---|
| Control | 576 ± 40 | 100 |
| 35S-DOG-3 | 170 ± 26 | 31 ± 6.0 |
| 35S-DOG-4 | 223 ± 18 | 40 ± 6.0 |
| 35S-DOG-8 | 103 ± 11 | 18 ± 3.0 |
| 35S-DOG-9 | 250 ± 24 | 45 ± 7.0 |
| 35S-DOG-11 | 283 ± 12 | 50 ± 5.0 |

Legend: Control, untransformed *Nicotiana tabacum* Var. *Samsun* NN plant; 35S-DOG, transgenic plants; the data are average values (n=4)±standard deviation.

EXAMPLE 8

Detection of the $DOG^R1$ Gene Mediated Resistance in the Progeny of Transgenic Tobacco Plants In order to detect the resistance of seedlings expressing the $DOG^R1$ gene seeds of the tobacco plants described in Examples 5 and 6 as well as seeds of untransformed tobacco plants were sterilized and placed on 0.05% 2-DOG containing MS medium. As shown in FIG. 7, the seedlings expressing the $DOG^R1$ gene under the control of the 35S promoter are vital after four weeks while the seedlings of the untransformed plants died at an early stage of development.

EXAMPLE 9

Detection of the $DOG^R1$ Gene Mediated Resistance in the Progeny of Potato Plants The construct described in Example 3 was transferred to potato plants *Solanum tuberosum* var. *Solara* by Agrobacteria-mediated transformation. The regenerated shoots were cultivated on selection-free medium. After six weeks the tips of the shoots were transferred to 0.05% 2-DOG containing MS medium. As shown in FIG. 8, the shoot of an untransformed plant has not grown after five weeks while the shoot expressing the $DOG^R1$ gene under control of the 35S promoter exhibits root and stem growth.

EXAMPLE 10

Production of Plasmid p35S Omega-$DOG^R1$ for the Transformation of Pea

In order to transform pea *Pisum sativum* a construct was prepared in pUC18 which contains the 35S promoter from Cauliflower Mosaic Virus, an untranslated transcription enhancer of the Tobacco Mosaic Virus U1 (Sonnewald (1992) Plant Journal 2 (4) 571), the $DOG^R1$gene and a transcription terminator OCS. This construct was introduced into the binary vector pGPTV (Becker (1992) PMB 20 1195) as EcoRI/HindIII fragment.

EXAMPLE 11

Selection of $DOG^R1$-transformed Pea Cells and Plant Regeneration on 2-DOG Containing Medium Sterile immature seeds of pea *Pisum sativum* were pre-cultivated for 2–3 days in liquid auxin/cytokinin-containing medium. Then longitudinal cuts of the embryonic axis were prepared and incubated for 1 hr in an overnight culture of *Agrobacterium tumefaciens*. The explants were then transferred to solid plant medium. After four days of incubation on modified B5 medium in diffused light at 22° C. the explants were washed and transferred to solid medium containing auxin/cytokinin and 0.075% 2-DOG. Selection was performed on various growth hormone concentrations with a permanent selection pressure of 0.075% 2-DOG. Regenerated shoots were grafted onto untransformed seedlings, transferred to soil and cultivated in the greenhouse.

EXAMPLE 12

Detection of the $DOG^R1$ Gene Mediated Resistance in Leaves of Pea Plants

The construct described in Example 10 was transferred to pea plants of *Pisum sativum* by Agrobacteria-mediated transformation. Calli of transformed and untransformed plants were placed on 0.075% 2-DOG containing medium. As shown in FIG. 10, the callus of untransformed plants did not develop Shoots while the callus developed after transformation with the $DOG^R1$ gene under the control of the 35S promoter developed shoots.

We claim:

1. A process for selecting a transformed plant cell, comprising the following steps:
   (a) obtaining a plant cell;
   (b) introducing a DNA sequence comprising a promoter active in plants and a sequence encoding a 2-deoxyglucose-6-phosphate (2-DOG-6-P) phosphatase operably linked thereto, or a vector comprising said DNA sequence into said plant cell, under conditions that allow expression of the 2-DOG-6-P phosphatase; and
   (c) selecting the successfully transformed plant cell on 2-deoxyglucose-containing media.

2. A process for selecting a transformed plant cell, comprising the following steps:
   (a) obtaining a plant cell;
   (b) introducing into said plant cell, under conditions that allow expression of 2-DOG-6-P phosphatase, DNA selected form the group consisting of:
      i) a recombinant DNA sequence comprising a promoter active in plants and a sequence encoding a 2-deoxyglucose6-phosphate (2-DOG-6-P) phosphatase operably linked thereto, and a further recombinant DNA sequence of interest;
      ii) a vector comprising said recombinant DNA sequence and said further recombinant DNA sequence of interest; and
      iii) a first vector comprising said recombinant DNA sequence and a second vector comprising said further recombinant DNA sequence of interest; and
   (c) selecting the successfully transformed plant cell on 2-deoxyglucose-containing media.

3. The process of claim 1 or 2, wherein the sequence encoding the 2-DOG-6-P phosphatase is selected from the group consisting of:
   (a) a DNA sequence which encodes the amino acid sequence of SEQ ID NO: 2;
   (b) a DNA sequence of SEQ ID NO: 1;
   (c) a DNA sequence which remains hybridized under wash conditions of 20 minutes at 55° C. in 6×SSC, 0.1% SDS and 20 minutues at 55° C. in 4×SSC, 0.1% SDS to a complementary strand of the DNA sequence of (a) or (b) and which encodes a polypeptide having 2-DOG-6-P phosphatase activity; and
   (d) a DNA sequence encoding a polypeptide having an amino acid sequence that is at least 90% identical to the amino acid sequence of SEQ ID NO: 2 and having 2-DOG-6-P phosphatase activity.

4. The process of claim 3, wherein the DNA sequence is obtained from yeast.

5. The process of claim 1 or 2, wherein the promoter is a 35S CaMV promoter.

6. The process of claim 2, wherein the further recombinant DNA sequance encodes a peptide, protein, antisense-RNA or sense-RNA, viral RNA or ribozyme.

7. The process of claim 1 or 2, wherein the vector is transferred to the plant cell via *Agrobacterium tumetaciens*.

8. The process of claim 1 or 2, wherein the DNA sequence or vector is transferred to the plant cell by particle bombardment.

9. The process of claim 1 or 2, wherein the DNA sequence further comprises a regulatory sequence selected from the group consisting of a transcription termination sequence, a polyadeiylation signal, or both, wherein said regulatory sequence is operably linked to the DNA sequence encoding said 2-deoxyglucose-6-phosphate phosphatase.

10. The process of claim 3, wherein the DNA sequence encodes the amino acid sequence of SEQ ID NO: 2.

11. The process of claim 3, wherein the DNA sequence is SEQ ID NO: 1.

* * * * *

SEQUENCE LISTING

<160> NUMBER OF SEQ ID NOS: 4

<210> SEQ ID NO 1
<211> LENGTH: 758
<212> TYPE: DNA
<213> ORGANISM: Saccharomyces cerevisiae

<400> SEQUENCE: 1

```
ggatcccc atg gca gaa ttt tca gct gat cta tgt ctt ttt gac cta gat        50
         Met Ala Glu Phe Ser Ala Asp Leu Cys Leu Phe Asp Leu Asp
         1               5                   10 ggt acc ata gtg agt aca aca gtg gcc gca gag aaa gca tgg acc aag         98
Gly Thr Ile Val Ser Thr Thr Val Ala Ala Glu Lys Ala Trp Thr Lys
15                  20                  25                  30 ttg tgt tac gaa tac ggt gtt gat cct tcc gag tta ttt aag cat tct        146
Leu Cys Tyr Glu Tyr Gly Val Asp Pro Ser Glu Leu Phe Lys His Ser
                35                  40                  45 cat ggt gca aga aca caa gag gtt ttg aga agg ttt ttc cct aaa ttg        194
His Gly Ala Arg Thr Gln Glu Val Leu Arg Arg Phe Phe Pro Lys Leu
            50                  55                  60 gat gat aca gac aat aaa ggt gtt ctt gct cta gaa aaa gat att gcc        242
Asp Asp Thr Asp Asn Lys Gly Val Leu Ala Leu Glu Lys Asp Ile Ala
        65                  70                  75 cat agt tac ttg gat aca gta agc ctt att cct ggt gca gag aac tta        290
His Ser Tyr Leu Asp Thr Val Ser Leu Ile Pro Gly Ala Glu Asn Leu
    80                  85                  90 ctg tta tcg tta gat gta gat act gag act caa aaa aag tta cct gaa        338
Leu Leu Ser Leu Asp Val Asp Thr Glu Thr Gln Lys Lys Leu Pro Glu
95                  100                 105                 110 agg aaa tgg gct atc gtt acc tct ggt tct cca tat ttg gca ttt tca        386
Arg Lys Trp Ala Ile Val Thr Ser Gly Ser Pro Tyr Leu Ala Phe Ser
                115                 120                 125 tgg ttc gag aca ata ttg aaa aat gtt gga aag ccc aaa gtt ttc att        434
Trp Phe Glu Thr Ile Leu Lys Asn Val Gly Lys Pro Lys Val Phe Ile
            130                 135                 140 act ggg ttt gac gtg aag aac ggt aag cct gat ccc gag ggt tat tca        482
Thr Gly Phe Asp Val Lys Asn Gly Lys Pro Asp Pro Glu Gly Tyr Ser
        145                 150                 155 aga gct cgt gat tta ttg cgt caa gat ttg caa tta act ggt aaa cag        530
Arg Ala Arg Asp Leu Leu Arg Gln Asp Leu Gln Leu Thr Gly Lys Gln
    160                 165                 170 gat ctg aag tat gtt gtc ttc gaa gat gca ccc gtg ggc ata aag gcc        578
Asp Leu Lys Tyr Val Val Phe Glu Asp Ala Pro Val Gly Ile Lys Ala
175                 180                 185                 190 ggc aaa gca atg ggc gcc att act gtg ggt ata aca tcc tcg tat gac        626
Gly Lys Ala Met Gly Ala Ile Thr Val Gly Ile Thr Ser Ser Tyr Asp
                195                 200                 205 aag agc gtt tta ttt gac gca gga gca gat tat gta gtc tgt gat ttg        674
Lys Ser Val Leu Phe Asp Ala Gly Ala Asp Tyr Val Val Cys Asp Leu
            210                 215                 220 aca cag gtt tcc gtg gtt aag aac aat gaa aac ggt att gtc atc cag        722
Thr Gln Val Ser Val Val Lys Asn Asn Glu Asn Gly Ile Val Ile Gln
        225                 230                 235 gta aac aac cct ttg aca agg gcc tgagtagtcg ac                          758
Val Asn Asn Pro Leu Thr Arg Ala
    240                 245
```

<210> SEQ ID NO 2
<211> LENGTH: 246

```
<212> TYPE: PRT
<213> ORGANISM: Saccharomyces cerevisiae

<400> SEQUENCE: 2

Met Ala Glu Phe Ser Ala Asp Leu Cys Leu Phe Asp Leu Asp Gly Thr
  1               5                  10                  15

Ile Val Ser Thr Thr Val Ala Ala Glu Lys Ala Trp Thr Lys Leu Cys
             20                  25                  30

Tyr Glu Tyr Gly Val Asp Pro Ser Glu Leu Phe Lys His Ser His Gly
         35                  40                  45

Ala Arg Thr Gln Glu Val Leu Arg Arg Phe Phe Pro Lys Leu Asp Asp
     50                  55                  60

Thr Asp Asn Lys Gly Val Leu Ala Leu Glu Lys Asp Ile Ala His Ser
 65                  70                  75                  80

Tyr Leu Asp Thr Val Ser Leu Ile Pro Gly Ala Glu Asn Leu Leu Leu
                 85                  90                  95

Ser Leu Asp Val Asp Thr Glu Thr Gln Lys Lys Leu Pro Glu Arg Lys
            100                 105                 110

Trp Ala Ile Val Thr Ser Gly Ser Pro Tyr Leu Ala Phe Ser Trp Phe
        115                 120                 125

Glu Thr Ile Leu Lys Asn Val Gly Lys Pro Lys Val Phe Ile Thr Gly
130                 135                 140

Phe Asp Val Lys Asn Gly Lys Pro Asp Pro Glu Gly Tyr Ser Arg Ala
145                 150                 155                 160

Arg Asp Leu Leu Arg Gln Asp Leu Gln Leu Thr Gly Lys Gln Asp Leu
                165                 170                 175

Lys Tyr Val Val Phe Glu Asp Ala Pro Val Gly Ile Lys Ala Gly Lys
            180                 185                 190

Ala Met Gly Ala Ile Thr Val Gly Ile Thr Ser Ser Tyr Asp Lys Ser
        195                 200                 205

Val Leu Phe Asp Ala Gly Ala Asp Tyr Val Val Cys Asp Leu Thr Gln
    210                 215                 220

Val Ser Val Val Lys Asn Asn Glu Asn Gly Ile Val Ile Gln Val Asn
225                 230                 235                 240

Asn Pro Leu Thr Arg Ala
                245

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 3
atggatcccc atggcagaat tttcagctga tctatg                            36

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 4
atgtcgacta ctcaggccct tgtcaaaggg ttg                               33
```